United States Patent
Treiber et al.

(10) Patent No.: US 10,641,776 B2
(45) Date of Patent: *May 5, 2020

(54) METHODS FOR MEASURING BINDING AND CELLULAR ENGAGEMENT OF LIGANDS WITH TARGET PROTEINS

(71) Applicant: EUROFINS DISCOVERX CORPORATION, Fremont, CA (US)

(72) Inventors: Daniel K. Treiber, San Diego, CA (US); Elena Menichelli, San Diego, CA (US)

(73) Assignee: Eurofins Discoverx Corporation, Fremont, CA (US)

( * ) Notice: Subject to any disclaimer, the term of this patent is extended or adjusted under 35 U.S.C. 154(b) by 8 days.

This patent is subject to a terminal disclaimer.

(21) Appl. No.: 15/932,335

(22) Filed: Feb. 16, 2018

(65) Prior Publication Data

US 2018/0275133 A1 Sep. 27, 2018

Related U.S. Application Data

(63) Continuation of application No. PCT/US2016/012356, filed on Jan. 6, 2016, which is a continuation-in-part of application No. 14/830,328, filed on Aug. 19, 2015, now Pat. No. 9,618,516.

(51) Int. Cl.
G01N 33/58 (2006.01)
G01N 33/542 (2006.01)

(52) U.S. Cl.
CPC ......... *G01N 33/581* (2013.01); *G01N 33/542* (2013.01); *H05K 999/99* (2013.01); *G01N 2333/938* (2013.01); *G01N 2500/04* (2013.01)

(58) Field of Classification Search
CPC ................................................ G01N 2500/04
See application file for complete search history.

(56) References Cited

U.S. PATENT DOCUMENTS

| | | |
|---|---|---|
| 6,828,099 B2 | 12/2004 | Michnick et al. |
| 8,945,853 B2 | 2/2015 | Raab et al. |
| 2002/0068298 A1 | 6/2002 | Tomich et al. |
| 2004/0137480 A1 | 7/2004 | Eglen |
| 2014/0045194 A1 | 2/2014 | Wehrman et al. |
| 2015/0133336 A1 | 5/2015 | Nordlund et al. |

FOREIGN PATENT DOCUMENTS

| | | |
|---|---|---|
| WO | 2010037718 | 4/2010 |
| WO | 2012143714 | 10/2012 |
| WO | 2013119579 | 8/2013 |

OTHER PUBLICATIONS

Graham et al. J of Biomolecular Screening, 2001, 6(6):401-411.*
Auld et al. (2015) "Examining Ligand-Based Stabilization of Proteins in Cells with MEK1 Kinase Inhibitors" Assay and Drug Develop. Tech., 13(5):266-276.
Kaniskan et al. (2015) "A Potent, Selective and Cell-Active Allosteric Inhibitor of Protein Arginine Methyltransferase? 3 (PRMT3)" Angewandte Chemie. Int. Ed., 54(17):5166-5170.
Patel et al. (2008) "ATLAS—A High-Throughput Affinity-Based Screening Technology for Soluble Proteins: Technology Application Using p38 MAP Kinase" Assay and Drug Develop. Tech., 6(1):55-68.
Schulze et al. (2014) "Cell-Based Protein Stabilization Assays for the Detection of Interactions between Small-Molecule Inhibitors and BRD4" J. of Biomol. Screening, 20(2):180-189.
Eglen et al. (2003) "Beta Galactosidase Enzyme Fragment Complementation as a Novel Technology for High Throughput Screening" Combinatorial Chemistry and High Throughput Screening, 6(4):381-387.
Koch et al. (2006) "Direct selection of antibodies from complex libraries with the protein fragment complementation assay" J. Mol. Biol., 357:427-441.
PathHunter Pathway Assay Cell Line & eXpress kit (2015) URL, http://web.archive.org/web/20150622015347/https:// www.cosmobio.co.jp/product/detail/drx_ph_pathway.asp?entry_id=10153.

* cited by examiner

*Primary Examiner* — Bin Shen
(74) *Attorney, Agent, or Firm* — Brian E. Davy; Bozicevic, Field & Francis LLP

(57) ABSTRACT

Disclosed are methods for detecting and quantitatively measuring a binding property of a compound to a target macromolecule, wherein the target macromolecule is subject to denaturation and is linked to a labeling peptide, such as a short enzyme fragment. The method uses a fluid mixture comprising (i) a chimeric molecule comprising a target macromolecule linked to the labeling peptide, wherein the target macromolecule may be a chimeric protein expressed by and within an intact viable cell and (ii) a compound being measured for binding to the target macromolecule, wherein said target macromolecule is subject to denaturation. After allowing for binding of the compound (e.g. a small molecule inhibitor of the target macromolecule), one detects a signal from the labeling peptide, such as by enzyme fragment complementation. This signal indicates a differential between denatured and non-denatured target macromolecules and thereby indicates a differential between target macromolecules not bound to the compound and target macromolecules bound to the compound, respectively.

23 Claims, 18 Drawing Sheets

Specification includes a Sequence Listing.

8A: Standard Denaturation Profile

8B: Pulse Denaturation Profile

METHODS FOR MEASURING BINDING AND CELLULAR ENGAGEMENT OF LIGANDS WITH TARGET PROTEINS

CROSS-REFERENCE TO RELATED APPLICATIONS

This application is a continuation of International Application No. PCT/US2016/012356, filed Jan. 6, 2016, which is a continuation-in-part of U.S. application Ser. No. 14/830,328, filed Aug. 19, 2015, issued as U.S. Pat. No. 9,618,516, which applications are incorporated herein by reference in their entireties.

REFERENCE TO SEQUENCE LISTING, COMPUTER PROGRAM, OR COMPACT DISK

The instant application contains a Sequence Listing which has been submitted as an ASCII text file and is hereby incorporated by reference in its entirety. This text file was created on Dec. 20, 2015, is named "3817_55_PCT_seq_list.txt" and is 4,096 bytes in size.

BACKGROUND OF THE INVENTION

Field of the Invention

The present invention relates generally to methods of monitoring binding of a compound to a target macromolecule, wherein the target macromolecule is either in vitro or expressed in a transfected cell, and the cell is not isolated or separated from the target macromolecule. The present invention also relates to a novel method of use of enzyme fragment complementation and using an enzyme fragment complementation assay that is used in a thermal shift assay.

Related Art

Presented below is background information on certain aspects of the present invention as they may relate to technical features referred to in the detailed description, but not necessarily described in detail. That is, individual compositions or methods used in the present invention may be described in greater detail in the publications and patents discussed below, which may provide further guidance to those skilled in the art for making or using certain aspects of the present invention as claimed. The discussion below should not be construed as an admission as to the relevance or the prior art effect of the patents or publications described.

A number of areas of biology and medicine depend on and develop assays to detect ligand binding to proteins and/or protein fragments. The binding assays help in determining a target which should be safe and druggable. The multibillion dollar pharmaceutical industry depends on these assays to find a drug compound that has an ability to bind to its target protein to perform its function.

A number of protein-ligand interaction assays have been developed and discussed in the past such as labeled and label-free ligand binding assays, structure-based ligand binding assays, thermodynamic ligand binding assays and whole cell ligand binding assays. Further, there is a fluorescence based ligand binding assay wherein a fluorescently labeled ligand binds to a target macromolecule. However, the assay is susceptible to different fluorescence interference and thus leads to undesirable alterations in the binding characteristics of the ligand. A radioactively labeled binding assay is popular for membrane based targets; however, the assay suffers from high cost along with hazards of handling high levels of radioactivity and thus comes with many restrictions for the lab and lab personnel working with the assay. NMR based analysis has also been applied to analyze the detailed structure of proteins and thus to assist in structure based drug design but suffers from a high cost of the assay and a long time required to analyze the spectra.

A previously developed thermal shift assay, also called differential scanning fluorimetry (DSF), is a thermal-denaturation assay that measures the thermal stability of a target protein and a subsequent increase in protein melting temperature upon binding of a ligand to the protein. The thermal stability change is measured by performing a thermal denaturation curve in the presence of a fluorescent dye, such as Sypro Orange. Such methods also involve a step of centrifugation and oil dispensing.

Thus, there is a need for a binding assay that offers a facile, sensitive and precise detection of ligand protein interaction, in a homogeneous assay format.

Specific Patents and Publications

U.S. Pat. No. 6,020,141, "Microplate thermal shift assay for ligand development and multi-variable protein chemistry optimization," issued Feb. 1, 2000 to Pantoliano et al., discloses a thermal shift assay that comprises contacting the target molecule with one molecule of a multiplicity of different molecules in each of a multiplicity of containers, simultaneously heating the multiplicity of containers, and measuring in each of the containers a physical change associated with the thermal denaturation of the target molecule.

Jung et al., "Affinity Map of Bromodomain Protein 4 (BRD4) Interactions with the Histone H4 Tail and the Small Molecule Inhibitor JQ1," J. Biol. Chem. Feb. 2, 2014, 289:9304-9319 discloses a thermal shift assay where BRD4 BD1 protein was mixed with 5 µl Sypro Orange (Molecular Probe).

Molina et al., "Monitoring Drug Target Engagement in Cells and Tissues Using the Cellular Thermal Shift Assay," Science 5 Jul. 2013: Vol. 341 no. 6141 pp. 84-87 discloses a method that takes advantage of a shift in protein thermal stability caused by drug binding to a target protein. The method was used to monitor drug target engagement in cancer cells and in mouse livers and kidneys. However, according to the authors, the method is not likely to work for highly inhomogenous proteins or for proteins in which unfolding of the ligand-binding domain does not promote aggregation.

BRIEF SUMMARY OF THE INVENTION

The following brief summary is not intended to include all features and aspects of the present invention, nor does it imply that the invention must include all features and aspects discussed in this summary.

The present invention comprises a method of measuring binding of a test compound to a target macromolecule. Further, the present invention discloses a homogeneous method of measuring binding of a test compound to a target protein of interest under heat denaturation of a macromolecule having a defined, native secondary and, optionally, tertiary structure, wherein the denaturation disrupts the secondary and/or tertiary structure of the target protein, but not a labeling peptide attached to it. The method may therefore be carried out in a homogenous format, without centrifugation or filtration steps between addition of the sample and readout of a result. The method will cause aggregation and a lack of accessibility of the labeling peptide attached to the target macromolecule; the labeling peptide may conveniently be added at the N or C terminus of the protein-based macromolecule. As will be described below, a number of short, relatively low temperature heat pulses are preferred to a single heat step; similarly, it is not preferred to completely denature a protein under study.

The present method may be carried out with the use of a whole cell, engineered to express a fusion protein containing the target macromolecule and the labeling peptide expressed in the cell from a vector introduced into the cell. Preferably the cell is a eukaryotic or mammalian cell. The compound of interest is incubated with a whole cell preparation and is heated with the whole cells, using heating conditions described below; some or all of the cells in the preparation are lysed at the step where a second label reacts with the labeling peptide, also as described below.

As explained below, the present invention as described above may be combined with a variety of steps and features described below. In certain embodiments, the invention comprises a step wherein detecting a signal indicates a differential between (i) denatured and (ii) non-denatured target macromolecules and thereby a differential between target macromolecules not bound to the compound and target macromolecules bound to the compound, respectively.

In one embodiment, the method comprises preparing a chimeric molecule that is a fusion protein comprising a labeling peptide and a protein target macromolecule. In another embodiment, the method comprises preparing a fusion protein comprising a nucleotide binding domain, labeling peptide and a target macromolecule. The nucleotide binding domain may be a DNA binding domain. The target macromolecule may be a protein, a peptide, a carbohydrate or a lipid molecule.

In other embodiments, the present invention is a method for measuring binding between a compound and a target macromolecule, comprising: (a) preparing a fluid mixture comprising (i) an intact viable cell expressing a chimeric protein that comprises a target macromolecule linked to a labeling peptide and (ii) a compound being measured for binding to the target macromolecule, wherein said target macromolecule is subject to denaturation; (b) incubating the fluid mixture of step (a) under conditions permitting binding of said compound to said target macromolecule; (c) partially denaturing target macromolecules in the fluid mixture, after incubating in step (b), under conditions that produce a combined mixture of (i) denatured chimeric molecules not bound to the compound and (ii) non-denatured chimeric molecules bound to the compound; and (d) contacting the combined mixture with a second label that binds to and reacts with the labeling peptide in the chimeric molecule to form a detectible signal, wherein, (e) the detectible signal in step (d) is dependent on denaturation of the target macromolecules and indicates a binding property between the compound and the target macromolecule in the chimeric protein.

In other embodiments, the present invention is a method as described above wherein said partially denaturing comprises heating the fluid mixture as prepared in step (b) in a step that is one of (a) multiple heating steps and at least one cooling step between heating steps and (b) a single heating step. In other embodiments, the present invention is a method as described above wherein the target macromolecule is a protein. In other embodiments, the present invention is a method wherein the protein further comprises an inactive exogenous polypeptide ("IEP") linked to the protein in a distal end from the labeling peptide. The protein would have the arrangement IEP-target protein-labeling peptide. In other embodiments, the present invention is a method as described above wherein the labeling peptide is between 10 and 100 amino acids in length.

In further embodiments, the present invention comprises a method wherein the labeling peptide is an enzyme fragment and the second label is a complementary enzyme fragment which combines with the labeling peptide to create an active enzyme (i.e. creating enzyme complementation) further comprising the step of lysing the viable cell. In further embodiments, the present invention comprises a method wherein the labeling peptide is an enzyme donor ("ED") active in enzyme fragment complementation of β-galactosidase and is fused to a terminus of a protein that is the target macromolecule. In other embodiments, the present invention comprises a method as described above wherein the ED is one of SEQ ID NO: 1, SEQ ID NO: 2, or SEQ ID NO: 3.

In other embodiments, the present invention is a method as described above wherein the labeling peptide is an epitope tag. In other embodiments, the present invention is a method as described above wherein the compound is a small molecule. In other embodiments, the present invention is a method as described above wherein the small molecule is one that binds to an active site on the target macromolecule.

In other embodiments, the present invention is a method as described above wherein the step of treating the fluid mixture comprises a step of heating the fluid mixture to a temperature that is one of between (a) 25° C. and 100° C., and (b) 30° C. and 60 C. In other embodiments, the present invention is a method as described above wherein a heating step comprises multiple heating steps for a defined period of time between 0.1 and 5 minutes. In other embodiments, the present invention is a method as described above wherein said heating step comprises applying heat to the mixture between 40° C. and 60° C., and further comprises multiple steps of heating for a time of 0.1 to 5 minutes. In other embodiments, the present invention is a method as described above wherein multiple steps of heating comprises an individual cooling step between individual heating steps, of between 10 seconds and 2 minutes in duration. In other embodiments, the present invention is a method as described above comprising between three and ten cooling steps. In other embodiments, the present invention is a method as described above wherein said temperature of the mixture during a cooling step remains greater than a temperature in a previous cooling step. In other embodiments, the present invention is a method as described above wherein said cooling steps comprise actively cooling the mixture.

In other embodiments, the present invention is a method as described above wherein the step of denaturation comprises at least one of (a) heating, (b) hydrostatic pressure, (c) an organic solvent and (d) radiation, whereby the cell remains intact after denaturation. In other embodiments, the present invention is a method as described above wherein the organic solvent is alcohol or chloroform.

In further embodiments, the present invention comprises a method as described further above, having steps (a) through (e), wherein steps (a) through (e) are repeated in mixtures containing different dilutions of said compound. In further embodiments, the present invention comprises a method as described further above, having steps (a) through (e), wherein repeated steps (a) through (e) may be used to calculate a binding constant ($K_D$) of binding of compound to the target macromolecule.

In further embodiments, the present invention comprises a method as described above wherein the target macromolecule is a protein which is one of a bromodomain protein, a protein kinase, a hydrolase, or a histone methyltransferase.

In other embodiments, the present invention is a method for measuring a binding property between a small molecule compound and a target protein, comprising: (a) preparing a fluid mixture comprising a cell expressing a chimeric protein that is a fusion of a target protein and a labeling peptide that is a β-galactosidase enzyme fragment of between 10 and 100 amino acids in length, said fluid mixture further containing a small molecule compound being measured for binding to the target protein; (b) incubating the fluid mixture of step (a) under conditions permitting binding of said small molecule compound to target proteins in the cell; (c) heating the fluid mixture of step (b) under conditions that cause denaturation of proteins not bound to the compound and also cause less denaturation of proteins bound to the compound, whereby one may detect a signal from proteins bound to the compound in step (c) by adding to the mixture a second label that is a β-galactosidase fragment that reacts with the labeling peptide on protein not denatured during the heating step(s), said mixture further comprising lysed cells. In other embodiments, the present invention is a method as described above wherein the assay mixture is prepared through steps (a) to (c) in a single container. This may be referred to as a homogeneous assay, not requiring any separation steps. In other embodiments, the present invention is a method as described above wherein replicate samples containing different concentrations of compound are prepared. In other embodiments, the present invention is a method as described above wherein the target macromolecule is one of a bromodomain protein and an enzyme.

In addition, the present invention comprises a kit. In further embodiments, the present invention comprises a kit comprising instructions for measuring binding of a potential ligand to a target protein, comprising components I through III, wherein component I is a target protein fused at a terminus to a first β-galactosidase enzyme fragment, component II is a β-galactosidase enzyme fragment that is complementary to the first β-galactosidase enzyme fragment, and component III is a β-galactosidase enzyme substrate, said instructions comprising instructions for: (a) preparing a fluid reaction mixture comprising a cell containing (i) a target protein fused at a terminus to a first β-galactosidase enzyme fragment (component I), and (ii) the potential ligand to the target protein; (b) heating the reaction mixture and cell of step (a) to cause at least some fraction of the target protein population to denature; (c) measuring, in the reaction mixture, after step (b), the amount of fusion protein that is not denatured in step (b), by adding to the mixture a β-galactosidase enzyme fragment that is complementary to the first β-galactosidase enzyme fragment (component II), and a substrate (component III) that indicates complementation of the β-galactosidase enzyme and indicates binding of the potential ligand as an inverse function of the heat step of step (b).

In further embodiments, the present invention comprises a kit wherein the target protein is a bromodomain protein and an enzyme wherein the enzyme may be one of a protein kinase, or a histone methyltransferase. In further embodiments, the present invention comprises a kit wherein the first β-galactosidase enzyme fragment is essentially identical to one of SEQ ID NO: 1, SEQ ID NO: 2, or SEQ ID NO: 3. In further embodiments, the present invention comprises a kit wherein said substrate is chromogenic, fluorescent, or chemiluminescent and which generates a signal in the presence of an active β-galactosidase but not inactive β-galactosidase.

BRIEF DESCRIPTION OF THE DRAWINGS

FIG. 8A shows a standard denaturation profile of 1 cycle, with a high temperature (45° C.)

over a time period of 3 minutes; FIG. 8B shows a pulse denaturation profile of 25 pulses at a reduced temperature of 40° C., where each pulse represents a brief denaturation pulse time of 7 seconds (i.e. a period of heating that is 7 seconds), where a PCR thermal cycler is reset to a lower temperature (e.g. ambient temperature) after a heating pulse.

Protein samples were exposed to a standard single heat denaturation step ("standard") or to repetitive 0.5 minute heat pulses. A 45° C. denaturation temperature was used for both protocols. "Total denaturation time" is the total amount of time that the protein sample was exposed to 45° C., so one single 3 minute step with the standard protocol (i.e. no pulsing, but a single 3 minute heating step at a constant temperature) is equivalent to 6 repetitive 0.5 minute steps with the pulse protocol. That is, six 0.5 heat pulses may be compared to one 3 minute heating step.

Figure 11:
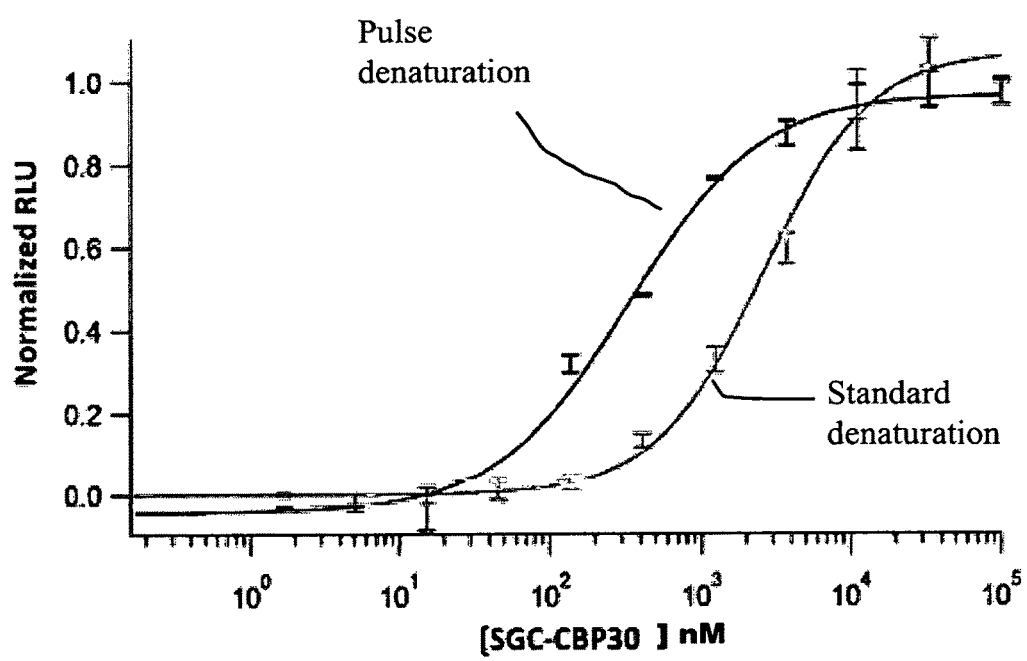

FIG. 11 is a graph showing different signals in RLU (relative luminosity units) comparing pulse denaturation versus standard denaturation for binding of SGC-CBP30 (a CREBBP/EP300-selective chemical probe), present at different concentrations, to CREBBP (Gene ID 1387, NCBI). SGC-CBP30 is commercially available from Tocris Biosciences, and is 8-(3-chloro-4-methoxy-phenethyl)-4-(3,5-dimethyl-isoxazol-4-yl)-9-(2-(morpholin-4-yl)-Dose response curves were measured for CREBBP with SGC-CBP30 with the "standard protocol" at 45° C. or with the "pulse protocol" at 40° C. Multiple cycles of gentle denaturation at 40° C. yielded apparent $EC_{50}$ values closer to the $K_D$ of 0.021 μM measured by Isothermal Titration calorimetry (see description of isothermal titration calorimetry in Picaud et al. "RVX-208, an inhibitor of BET transcriptional regulators with selectivity for the second bromodomain," PNAS Dec. 3, 2013 vol. 110 no. 49: 19754-19759). The gentle denaturation is less than the melting point of CREBBP, which is 46° C.

Figure 12:
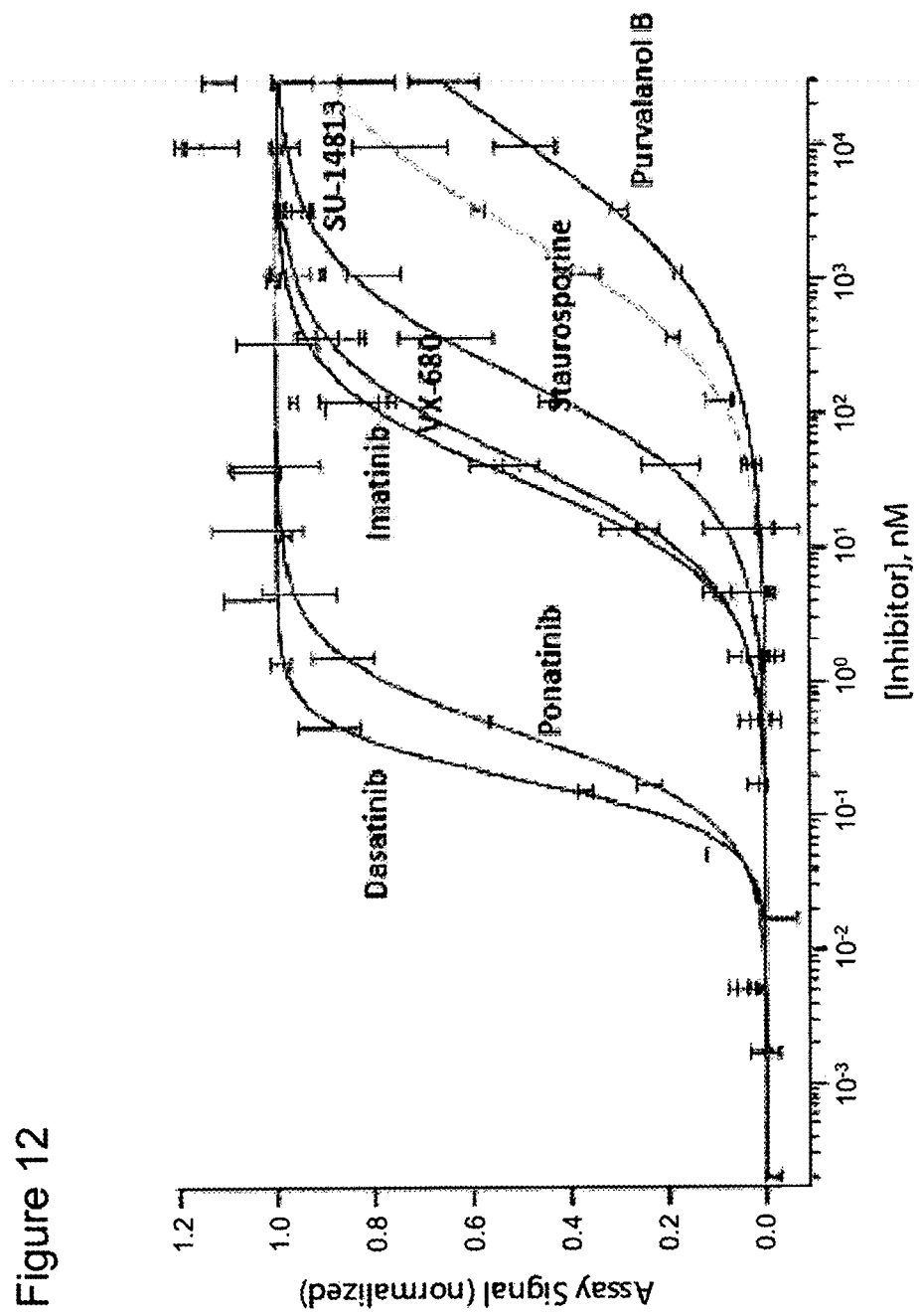

FIG. 12 is a graph showing dose response curves for seven inhibitors of the ABL1 protein kinase. The dose response curves were obtained using ED-tagged ABL1 and the inhibitors in a pulse denaturation protocol. It shows, for example, that one compound tested, dasatinib (N-(2-chloro-6-methylphenyl)-2-[[6-[4-(2-hydroxyethyl)-1-piperazinyl]-2-methyl-4-pyrimidinyl]amino]-5thiazolecarboxamide, monohydrate), binds to the test protein, ABL1, to a significant degree at a 1 nM concentration, whereas other compounds, such as imatinib (4-[(4-methylpiperazin-1-yl) methyl]-N-[4-methyl-3-[(4-pyridin-3-ylpyrimidin-2-yl) amino]phenyl]benzamide), do not bind at 1 nM to a significant effect, as measured by the present heat pulse assay. Very significant differences among different inhibitors were easily visualized.

Figure 13:
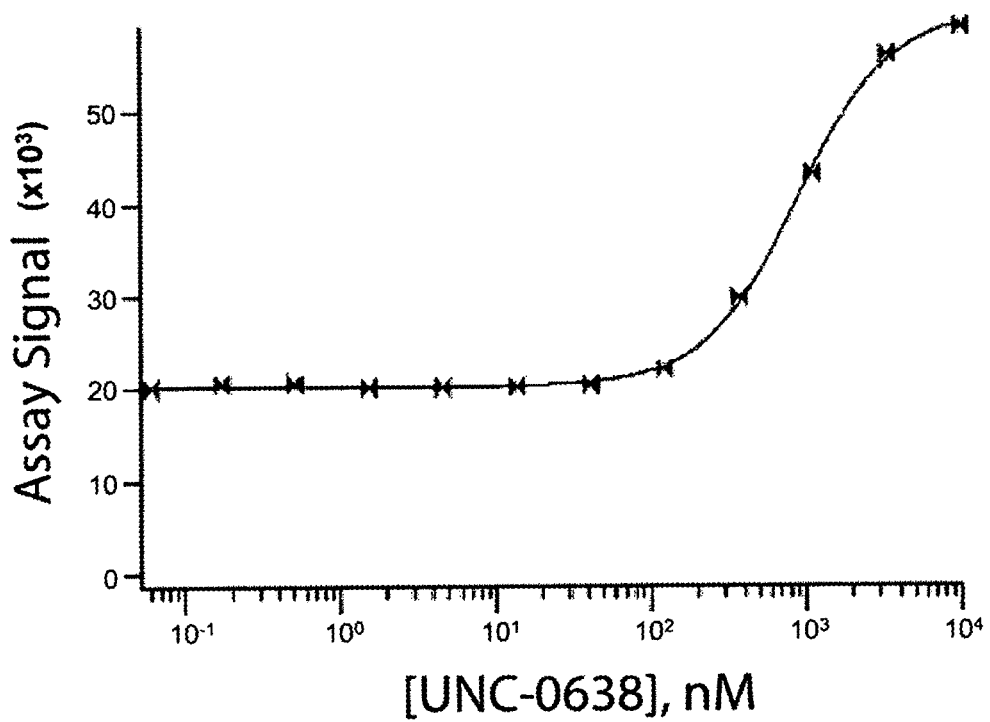

FIG. 13 is a graph showing a dose response curve for UNC-0638 (2-Cyclohexyl-6-methoxy-N-[1-(1-methylethyl)-4-piperidinyl]-7-[3-(1-pyrrolidinyl)propoxy]-4-quinazolinamine, CAS 1255580-76-7), an inhibitor of the G9a protein methyltransferase. The dose response curve was obtained using ED-tagged G9a and the inhibitor in a pulse denaturation protocol.

Figure 14:
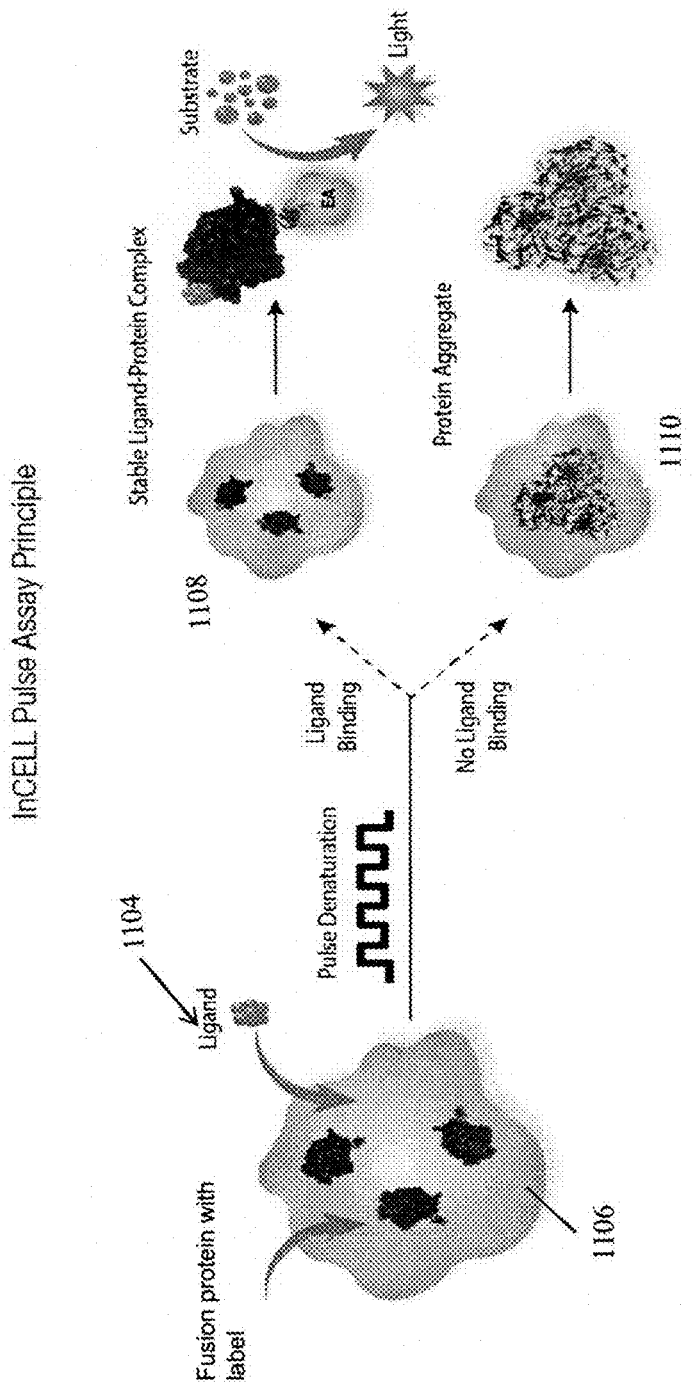

FIG. 14 is a schematic representation of an in-cell embodiment of the present assay, showing a cell 1106 transfected with an enzyme fragment tagged protein of interest; the cell has been modified to overexpress a fusion protein comprising a peptide label (PL small enzyme fragment of β galactosidase) and a target macromolecule. The cell is incubated with a potential ligand 1104, which can cross the plasma membrane of the cell. The compound is being evaluated for binding to the protein of interest. The cell and ligand are then subjected to pulse denaturation as described above. To the extent that the tagged macromolecule (e.g. a fusion protein/nucleic acid and labeling peptide) in the cell binds to the test, compound, it is protected from denaturation, as shown at 1108, and the PL can react with the EA (enzyme acceptor, i.e. large fragment of β-galactosidase to form an active β-galactosidase enzyme that, as shown here, will produce a luminescent readout ("light"). In cells in which the tagged macromolecule did not bind to the test ligand (or if the test compound cannot cross the plasma membrane), a protein aggregate is formed; reduced signal will be produced by the substrate. The binding and non-binding status, shown at 1108 and 1110, respectively, are present in a state of disequilibrium, and a binding curve can be constructed with different concentrations of test compound that are bound to the tagged macromolecule expressed in the recombinant cell. The present methods may also be used to evaluate the ability of a test compound to cross the plasma membrane of an engineered cell as described. This provides information regarding bioavailability as well as binding properties.

Figure 15:
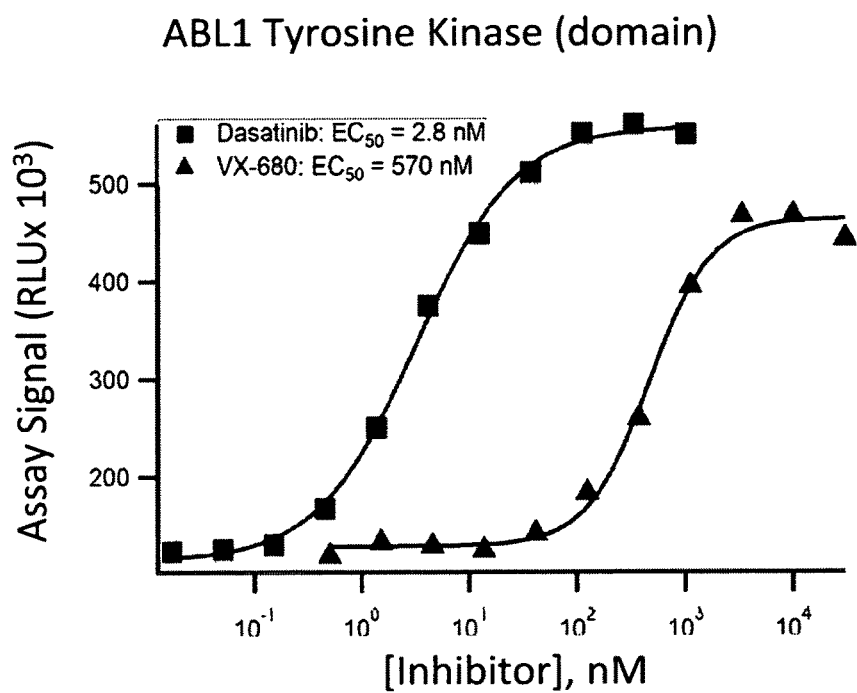

FIG. 15 shows an exemplary in-cell pulse assay using inhibitors Dasatinib and VX-680 tested for binding to ABL1 tyrosine kinase.

Figure 16:
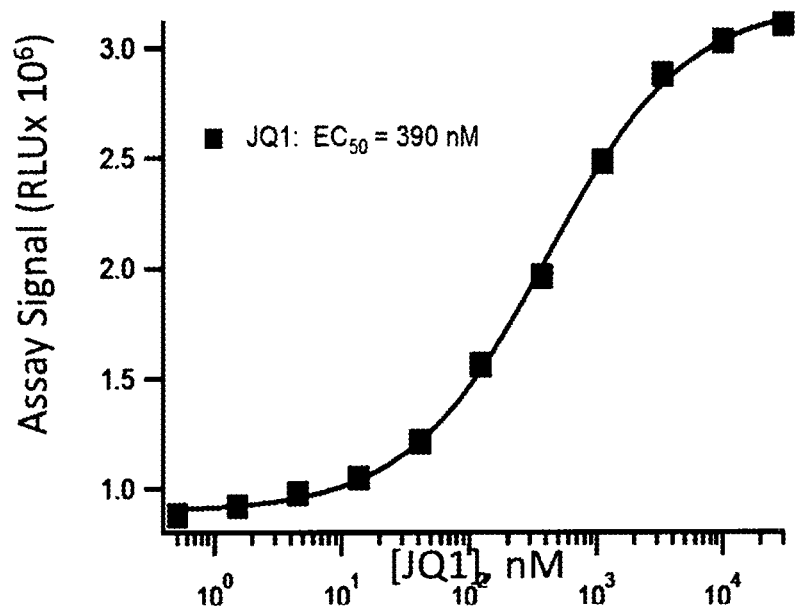

FIG. 16 shows an exemplary in-cell pulse assay using inhibitor JQ1 on BRD4(1) bromodomain.

Figure 17:
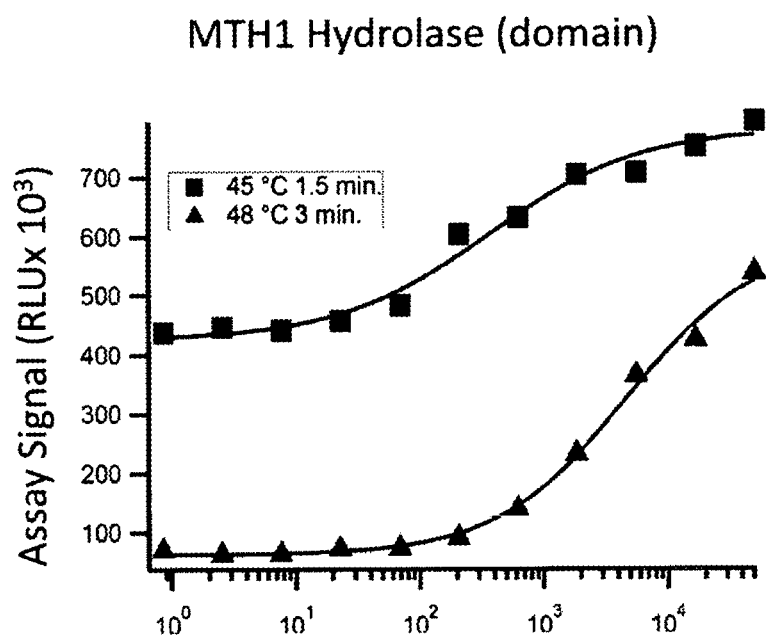

FIG. 17 shows an exemplary in-cell pulse assay using MTH1 hydrolase domain and inhibitor SCH 51344 using two preliminary denaturation protocols indicated in the legend.

Figure 18:
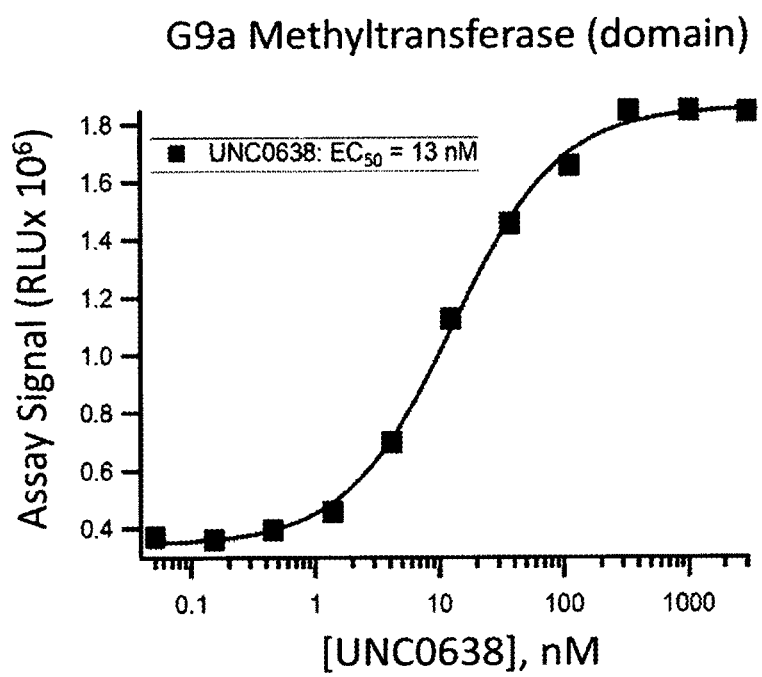

FIG. 18 shows an exemplary in-cell pulse assay using G9a methyltransferase catalytic domain and inhibitor UNC0638.

DETAILED DESCRIPTION

Definitions

Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, the preferred methods and materials are described. Generally, nomenclatures utilized in connection with, and techniques of, cell and molecular biology and chemistry are those well-known and commonly used in the art. Certain experimental techniques, not specifically defined, are generally performed according to conventional methods well known in the art and as described in various general and more specific references that are cited and discussed throughout the present specification. For purposes of clarity, the following terms are defined below.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A laboratory Manual (1982); "DNA Cloning: A Practical Approach", Volumes I and II (D. N. Glover ed. 1985); "Oligonucleotide synthesis" (M. J. Gait ed. 1984); "Nucleic Acid Hybridization" (B. D. Hames & S. J. Higgins eds. (1985)); "Transcription and Translation" (B. D. Hames & S. J. Higgins eds. (1984)); "Animal Cell Culture" (R. I. Freshney, ed. (1986)); "Immobilized Cells and Enzymes" (IRL Press, (1986)); B. Perbal, "A Practical Guide to Molecular Cloning" (1984).

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely", "only" and the like in connection with the recitation of claim elements, or use of a "negative" limitation.

Ranges: For conciseness, any range set forth is intended to include any sub-range within the stated range, unless otherwise stated. As a non-limiting example, a range of 2 minutes to 8 minutes includes 3-4 minutes, 2-7 minutes, etc. A temperature range of 40-45° C. includes 41-45° C., 42-43° C., etc. The term "about" has its ordinary meaning of approximately and may be determined in context by experimental variability. In case of doubt, the term "about" means plus or minus 5% of a stated numerical value.

As will be apparent to those of skill in the art upon reading this disclosure, each of the individual embodiments described and illustrated herein has discrete components and features which may be readily separated from or combined with the feature of any of the other several embodiments without departing from the scope or spirit of the present invention. Any recited method can be carried out in the order of events recited or in any other order which is logically possible.

The term "peptide" as used herein refers to any polymer compound produced by amide formation between an α-carboxyl group of one amino acid and an α-amino group of another group. As used herein, a peptide may be a labeling peptide, of relatively small size, having little or no secondary structure (i.e. a loop) linked to a macromolecule and for detecting the fusion.

The term "protein" as used herein refers to polypeptides of specific sequence of more than about 50 residues. While all proteins are peptides, the term "peptide" generally refers to a fragment of a protein; the term "fusion protein" is used to refer to both fusion proteins and fusions with peptides, such as a fusion with a labeling peptide, e.g. an ED. In connection with the present assay, it will be understood that the protein under study need not be a full length protein sequence. The target macromolecule may in fact be a protein that has been truncated to isolate a domain under study, modified for easier handling, etc. Thus a protein fragment in the present assay is referred to for simplicity as a "protein".

The term "fusion protein" as used herein refers to a protein created through genetic engineering from two or more proteins/peptides. In general, this is achieved by creating a "fusion gene", a nucleic acid that encodes the fusion protein. For example, a fusion gene that encodes a fusion protein may be made by removing the stop codon from a first DNA sequence encoding the first protein, then appending a DNA sequence encoding the second protein in frame. The resulting fusion gene sequence will then be expressed by a cell as a single fusion protein. Fusion proteins may include a linker (or "spacer") sequence which can promote appropriate folding and activity of each domain of the fusion protein. Fusion proteins may also include epitope tags (labeling peptide) for identification (e.g., in western blots, immunofluorescence, etc.) and/or purification. Non-limiting examples of epitope tags in current use include: HA, myc, FLAG, and 6-HIS. These known epitope tags are relatively short peptides that can be specifically detected by monoclonal antibodies, i.e. a second label that binds to the epitope tag attached to the target macromolecule.

The fusion protein will be "chimeric" if the molecule contains two sequences that are not normally found together in the same polypeptide chain. A chimeric molecule may also contain a fusion of two different polymers, such as a single polypeptide chain comprising the target macromolecule and the labeling peptide. The chimeric molecule may also contain a labeling peptide chemically linked to the target macromolecule. A chimeric molecule as defined may contain a target macromolecule linked or fused to a labeling peptide, and further wherein said target macromolecule is fused or linked to a third polypeptide that is used to increase the effective concentration of the target macromolecule when partial denaturation and detection are carried out.

For purposes of the present invention, a protein used in the assay will often be a human protein of interest as a drug target, and will be prepared by recombinant methods in an active form and containing known protein binding sites. However, the present definition of "protein" specifically includes fragments of proteins that are not full length proteins, but contain only a fragment of sufficient structure to have the requisite secondary and tertiary structure and have the binding site to the compound of interest.

The term "target macromolecule" as used herein refers to various macromolecules that can be denatured. That is, they have a secondary or tertiary structure that can be eliminated by heat, or, alternatively, other agents. They are, for example DNA, RNA, and/or proteins (which includes protein fragments such as protein domains). In some cases, the "macromolecule" may be of a relatively small MW compared to a full length protein, provided that it has a native three dimensional structure that is rigidly defined by cross linking, hydrogen binding or the like. For example, knottin small peptides have a rigid, defined tertiary structure that could be measured by the present assay. The term "macromolecule" refers to a polynucleotide, polypeptide or a complex carbohydrate having a defined tertiary structure. For example, glycans, often present as glycoproteins or glycolipids, form highly complex structures. In mammals ten monosaccharides are utilized in building glycoconjugates in the form of oligo- (up to about a dozen monomers) and polysaccharides.

The present "macromolecule" is one that can be denatured by destroying in significant part such three dimensional structure. A "target" macromolecule is a macromolecule capable of binding specifically to a third molecule, typically a small molecule or other pharmaceutical drug candidate. The target macromolecule used in the present assays may be purified, present in a cell extract, or in other forms. A target macromolecule may have a specific binding partner in nature, and a small molecule is intended to target this binding.

The term "small molecule" is art-recognized and refers to a composition which has a molecular weight of less than about 2000 amu, or less than about 1000 amu, and even less than about 500 amu. Small molecules may be, for example, nucleic acids, peptides, polypeptides, peptide nucleic acids, peptidomimetics, carbohydrates, lipids or other organic (carbon containing) or inorganic molecules. Many pharmaceutical companies have extensive libraries of chemical and/or biological mixtures, often fungal, bacterial, or algal extracts, which can be screened with any of the assays of the invention. The term "small organic molecule" refers to a synthetic or purified natural small molecule that is often identified as being an organic or medicinal compound, and does not include molecules that contain nucleic acids, peptides or polypeptides.

The term "binding" as used herein refers to the binding of small molecules, proteins or compounds to the proteins in a cell or in a solution. The terms "binding partner" or "member of a binding pair" refer to molecules that specifically bind other molecules to form a binding complex such as antibody-antigen, lectin-carbohydrate, nucleic acid-nucleic acid, biotin-avidin, etc. In particularly preferred embodiments, the binding is predominantly mediated by non-covalent (e.g. ionic, hydrophobic, etc.) interactions and is between a small molecule and its target and/or two proteins that specifically bind to each other during a cellular process.

The term "enzyme fragment complementation (EFC)", as explained below, involves the use of one enzyme fragment, which may be referred to as a labeling peptide or an ED (enzyme donor), which is not enzymatically active until it is complexed with another enzyme fragment, termed an EA, or enzyme acceptor, or second label. The terms ED and EA are used with reference to β-galactosidase. However, the term EFC or labeling peptide is not limited to a β-galactosidase system. EFC is a generic term to describe the combination of enzyme fragments to form active enzyme, followed by detection of that activity by measurement of a hydrolysis product, generally by colorimetric, fluorometric or chemiluminescent methods. It has the advantage of providing an amplification step, due to enzyme turnover, as part of the detection system.

By way of illustration, EFC assays based either on dihydrofolate reductase or beta-lactamase have been used to quantify the effects of the drug rapamycin on its target in living cells (Remy, I. and Michnick, S. W., Clonal Selection and In Vivo Quantitation of Protein Interactions with Protein Fragment Complementation Assays. Proc Natl Acad Sci USA, 96: 5394-5399, 1999; Galarneau, A., Primeau, M., Trudeau, L.-E. and Michnick, S. W., A Protein fragment Complementation Assay based on TEM1 ß-lactamase for detection of protein-protein interactions, Nature Biotech. 20: 619-622, 2002) and to study phosphorylation-dependent interactions of two domains of the cyclic AMP response element binding protein, CREB (J M Spotts, R E Dolmetsch, & M E Greenberg, 2002, Time-lapse imaging of a dynamic phosphorylation-dependent protein-protein interaction in mammalian cells, Proc. Natl. Acad. Sci. USA 99: 15142-15147.).

Another example of EFC useful here is Promega NanoBiT™. This technology employs a NanoLuc, a small (19 kDa) luciferase enzyme engineered for structural stability and the ability to generate an intense, steady, bioluminescent signal. Details are described in Dixon et al., "NanoLuc Complementation Reporter Optimized for Accurate Measurement of Protein Interactions in Cells," ACS Chem. Biol., Just Accepted Manuscript, Publication Date (Web): Nov. 16, 2015. By design, the NanoBiT subunits (i.e., 1.3 kDa peptide, 18 kDa polypeptide) weakly associate so that their assembly into a luminescent complex is dictated by the interaction characteristics of the target proteins onto which they are appended.

The term "labeling peptide" means a peptide having essentially no secondary structure (i.e. random coil) and which functions as a label for detection of a protein or protein fragment (e.g. target peptide) fused thereto and having essentially no effect on the stability of the target peptide to which it is fused. The labeling peptide will generally be less than 100 amino acids in length. It may itself function as a label, or it may provide an epitope for antibody recognition. As explained below, the labeling peptide is selected so as not to affect the stability of a fusion partner of the labeling peptide.

The term "ED", as is known in the art, means an enzyme donor fragment for use in a β-galactosidase enzyme fragment complementation assay. Examples of EDs are given below. An ED that is "essentially identical" to one of SEQ ID NOs: 1-3 will be 100% identical except for up to two amino acid alterations.

The term "EA", as is known in the art, means an enzyme acceptor fragment for use in a β-galactosidase enzyme fragment complementation assay.

The term "denaturation" is used in its conventional sense to refer to a process in which proteins, nucleic acids or other macromolecules or macromolecular structures (e.g. ribosomes) lose their quaternary structure, tertiary structure and or secondary structure, at least in part. Loss of this native state in the present method occurs by application of some external stress or compound such as a strong acid or base, a concentrated inorganic salt, an organic solvent (e.g., alcohol or chloroform), radiation or heat. The term used here specifically includes partial denaturation, where only a fraction of the molecules (e.g. proteins) in a mixture are denatured. The term protein "melting," which refers to protein denaturation, is also used herein. As is known, a melting temperature (Tm) may be determined from a protein denaturation study. See, for details, US 2013/0217137.

The term "pulse denaturation" refers to a process in which proteins or nucleic acids denature by application of more than one cycle of a short heat pulse which is followed by short re-equilibrium at room temperature or below room temperature. A "mild temperature" is considered to be a temperature at least about 5° C. less than the melting temperature of the macromolecule being heated. A protein melting point can be determined by known methods, as in e.g. US 20140057368, referred to below. A pulse denaturation protocol may cause a small amount of denaturation in a given step (5%-10%). However, the denaturation is cumulative over multiple cycles, and may reach 80% or more denaturation after the pulses are applied. By way of example, a pulse denaturation protocol may comprise 10-70 pulses at 37-50° C. for 5-10 seconds, separated by 15-20 second cooling pulses. As shown below, the pulse denaturation may be carried out under conditions where the fraction of the protein denatured in one cycle does not refold when cooled or upon additional pulse denaturation steps.

The term "protein denaturation" refers to denaturation of proteins involving the disruption and possible destruction of both the secondary and tertiary structures.

Denaturation disrupts the normal alpha helix and beta sheets in a protein and uncoils it into a random shape resulting in precipitation or coagulation of the protein. Denaturation of proteins results in loss of their biological function and/or activity. Denaturation may occur by some external stress or compound such as a strong acid or base, a concentrated inorganic salt, an organic solvent, radiation, heat or cold. Denaturation can be complete or partial but, for the present purposes, is sufficient to cause insolubility. Pressure denaturation of proteins is described, e.g. in Johnson et al., "Pressure and Protein Denaturation," J. Biol. Chem. 1946, 163:689-698. Frick, "Effect of Ionizing Radiation on Protein Denaturation," Nature 169, 965-966 (7 Jun. 1952) describes the use of ionizing radiation to denature solutions of proteins.

The term "inactive exogenous polypeptide" or "inactive exogenous polypeptide sequence" refers to a sequence engineered to be expressed in a chimeric protein used in the present methods that is added to provide additional sequence to the fusion protein without participating in or affecting the binding events in the assay. It is used to modulate the denaturation of the chimeric protein. This polypeptide may be of any length, e.g. 20-1000 amino acids long and is exogenous in the sense that it is not part of the fusion protein unless artificially coded, and, furthermore, it does not participate in binding of the peptide label to the second label. In addition, it does not bind to the compound of interest.

The term "thermal stability" refers to a quality of a macromolecule such as a protein to resist irreversible change in its chemical or physical structure at a high relative temperature.

The term "thermal shift assay" refers to an assay based on the principles that a purified protein will denature and unfold at a particular temperature and that the binding of a ligand to a protein will thermally stabilize the protein. Further details on carrying out various thermal shift assays may be found in Nordlund, US 20140057368, "Methods for determining ligand binding to a target protein using a thermal shift assay." As described there, such assays may be carried out with non-purified samples.

The term "homogenous" is used in its standard sense, to refer to an assay format and method that does not require a separation step. This allows measurement of results by a simple mix and read procedure, without the need to process samples by separation or washing steps during the assay.

Overview

It is well established that ligand binding protects proteins from thermal denaturation, and this concept has been exploited to measure drug-target interactions in both cellular and solution milieus ("Cellular Thermal Shift Assay"; "CETSA") (Science (2013), cited above). CETSA is based on the principle that denatured proteins aggregate into complexes that can be removed by centrifugation, and subsequent publications by this same group and other groups have shown that this concept can be applied to both intracellular proteins and integral membrane proteins (See, Reinhardt et al., "Thermal proteome profiling monitors ligand interactions with cellular membrane proteins," Nature Methods 12, 1129-1131 (2015)). There, extended thermal proteome profiling to detect transmembrane protein-small molecule interactions in cultured human cells is described. When they assessed the effects of detergents on ATP-binding profiles, the authors observed shifts in denaturation temperature for ATP-binding transmembrane proteins. Aliquots were heated to different temperatures, digested, 10-plex tandem mass tag (TMT10) labeled and analyzed by mass spectrometry.

The present methods can be used to measure other binding interactions, such as described in Huber et al., "Proteome-wide drug and metabolite interaction mapping by thermal-stability profiling," Nature Methods 12, 1055-1057 (2015). There, the authors show that in combination with quantitative mass spectrometry, the approach allows for the systematic survey of protein engagement by cellular metabolites and drugs. The authors profiled the targets of the drugs methotrexate and (S)-crizotinib and the metabolite 2'3'-cGAMP in intact cells and identified the 2'3'-cGAMP cognate transmembrane receptor STING, involved in immune signaling.

It should be noted, however, that this prior art method requires that denatured-aggregated proteins are removed by an impractical high g-force centrifugation step and that the soluble protein protected at high temperature by ligand binding is quantified by cumbersome, relatively imprecise, and low linear dynamic range assays such as Western blot, ELISA, and mass spectroscopy. Most reported, CETSA data have been collected on natively expressed proteins present at natural levels in a given cell-line or tissue; however, in at least one report, membrane proteins expressed as fusions to Green Fluorescent Protein (GFP) have been described [Structure 20, 1293-1299, Aug. 8, 2012]. In this study the GFP component of the fusion protein was used to detect the protein during analytical size-exclusion chromatography, and was not used to directly assess the structural state of the protein.

The present invention relates to a patent application by the present inventors, entitled "Homogeneous Thermal Ligand Binding Assay", cited herein as a related patent application. It describes a biochemical (in vitro, not intracellular) method for using recombinant target proteins fused to a short "Enzyme Donor" (ED) peptide derived from beta-galactosidase for detection of ligand-protected target protein after heat denaturation. The ED peptide (a.k.a. ProLabel™ enzyme donor or PL) can be detected at femtomolar concentrations in homogeneous assays by the simple addition of the beta-galactosidase Enzyme Acceptor (EA) protein, which complements ED in trans leading to robust beta-galactosidase enzyme activity (Enzyme Fragment Complementation (EFC)). This detection system is not only sensitive but also has a linear dynamic range of 4-5 orders of magnitude. In addition, ED-labeled proteins that denature/ aggregate due to thermally-induced unfolding are significantly less competent to complement EA and are thus less active in this format. As such, with ED-labeled proteins, the impractical centrifugation step required in the Science paper cited above is not required, nor are immuno-assay or mass spectroscopy-based readouts. Furthermore, the invention is distinguished from the use of GFP fusions (see citation above) that simply act as a detection tag, since the ED tag in our system is both a detection tag and also reports on the folded state of the protein.

The use of recombinant ED-labeled proteins (either purified or in crude cell extracts, and potentially in a cellular milieu) thus addresses all of the procedural bottlenecks described above for current thermal-denaturation-based ligand screening methods: 1. No requirement for pure protein; 2. Low target protein concentrations required (<10 nM); 3. Assay simplicity, sensitivity, dynamic range, and precision (homogeneous EFC reaction versus immune-assay); 4. Assay throughput (no centrifugation step or immuno-assays required).

The methods described herein can be applied to target macromolecules, such as proteins, in a cellular milieu. That is, the target macromolecule can be expressed within a cell (or cells in a tissue), preferably a mammalian cell, and then the compound can be exposed to the cell in an intact state, i.e. crossing the intact plasma membrane. The present method of heat denaturation in the presence of a test compound can be carried out while the target molecule and compound are contained in a living cell. The term "in" a cell is used broadly to refer to a target macromolecule that is entirely inside a cell, e.g. in the cytosol, nucleus, internal membrane, etc. or a macromolecule that is attached to the plasma membrane of the cell. In this case, the target molecule may have an extracellular domain. The present method, which is being developed commercially under the name "InCELL Pulse"™ system, comprises heating of cells to produce a thermal shift in enzyme complementation, as exemplified in FIGS. 14-18. The InCELL Pulse system can quantitatively detect intracellular binding of small molecule ligands to cytosolic target protein domains expressed as ED-enzyme fragment (e.g. PL) fusions, and has been demonstrated with multiple target classes, including kinases, bromodomain proteins, methyltransferases, and hydrolases. This method can also be applied to integral membrane proteins, for which cellular penetration of the test ligand may or may not be required to achieve target engagement.

Furthermore, the present Examples 13-16 use single heat pulses as opposed to a series of short heat pulses (pulse denaturation), which is used in previous examples herein. Also, the cell-free biochemical application of this technology (e.g. Examples 8-11) has been demonstrated by use of an N-terminal fusion of the target protein to the NFκB DNA binding domain (Examples not shown). The addition of an extra amino acid sequence (termed below an "inactive exogenous polypeptide") enhances assay performance in some cases. It is expected that the NFκB moiety can be more critical for the cell-free assays (e.g. Examples 8-11) than for the cellular assays (e.g. Examples 13-16), but likely will have benefit in some InCELL Pulse assays. The inactive exogenous polypeptide may be linked to an N terminus of the target macromolecule (protein) and the labeling peptide may be linked to the C terminus of the target macromolecule.

The present method monitors and measures a binding property between a compound and a target macromolecule. It exploits the known ability of ligands such as small molecules to protect macromolecules such as proteins from denaturation and aggregation due to unfolding and shows that this method can be applied to evaluation of ligands within a whole cell, e.g. a mammalian cell that has been transfected with a chimeric protein. Prior art methods have required high-g-force centrifugation steps and insensitive readouts. The present methods, exemplified by the use of β-galactosidase enzyme fragment complementation, utilize a small peptide (less than 100 amino acids) fused to the macromolecule. The small peptide may be the known enzyme donor, the ProLabel™ enzyme donor ("ED") commercially available from DiscoveRx Corporation, Fremont Calif. Enzyme fragment complementation provides a sensitive, facile generic readout. Moreover, the assay may be carried out in a homogeneous format, meaning that no physical separation of the reagents is required, eliminating the need for filtration, decanting, centrifugation, etc. The present invention is widely applicable to a number of ligand binding assays.

The ligand may typically be a small molecule that is under study for binding properties to a target molecule, which will be a macromolecule that is susceptible to thermal denaturation and resultant loss of buoyancy or stability in a fluid. The binding property may be measured in the presence of a competitor or under different target macromolecules. The invention is illustrated, but not limited, by a study of BRD4 (bromodomain-containing protein 4). As demonstrated here, the present methods provide:

1. Generic homogeneous direct ligand binding assay;
   Simple, rapid method (no wash, filtration, or centrifugation steps)
   No protein purification required
   No fluorescent labels or antibodies
   Target protein present at <10 nM (in vitro embodiment)
   Exploits DiscoveRx's proprietary Enzyme Fragment Complementation (EFC) technology
2. BRD4(1) working example
   Highly precise (median % CV (coefficient of variance ~0.5); outstanding signal to noise ratio
   Correct rank order for high and low potency inhibitors
3. Applications
   High throughput screening (384-well compatible)
   Hit confirmation & potency rank order
4. Target classes
   Bromodomains; proteins of pharmaceutical interest, such as kinases, G protein-coupled receptors, methyltransferases, RAS, MAPK, and MSK1 signaling molecules, nuclear receptors, ion channels, methyltransferase, nucleoside hydrolase, etc. Preferred target classes are human drug targets.

Figure 1:
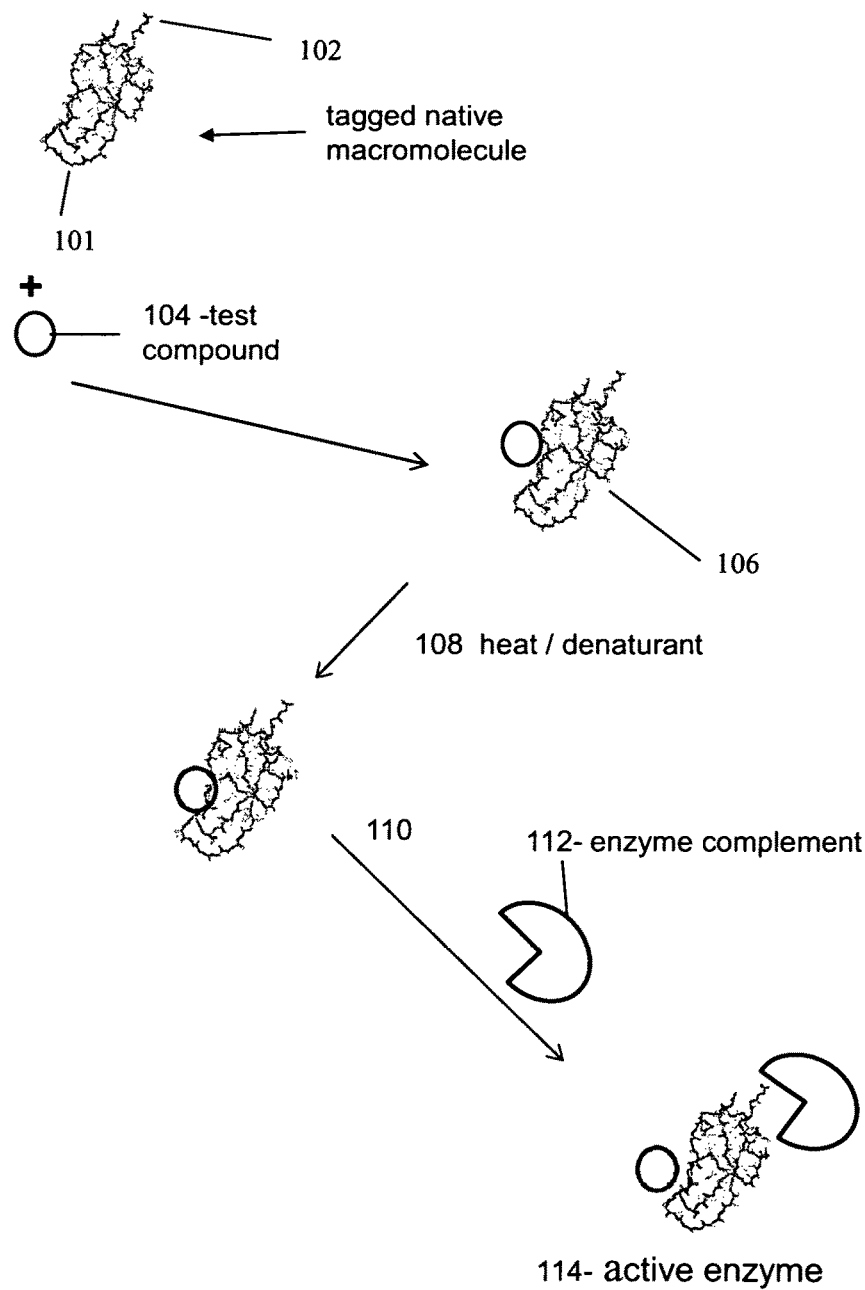
FIG. 1 is a schematic representation of the present assay showing how a tagged macromolecule (e.g. a fusion protein and labeling peptide) is in native form (i.e. native secondary and tertiary structure) protected from denaturation in the presence of a test compound that binds to the tagged native macromolecule; the protection therefore enables detection of the binding with an enzyme complementation assay.
Figure 2:
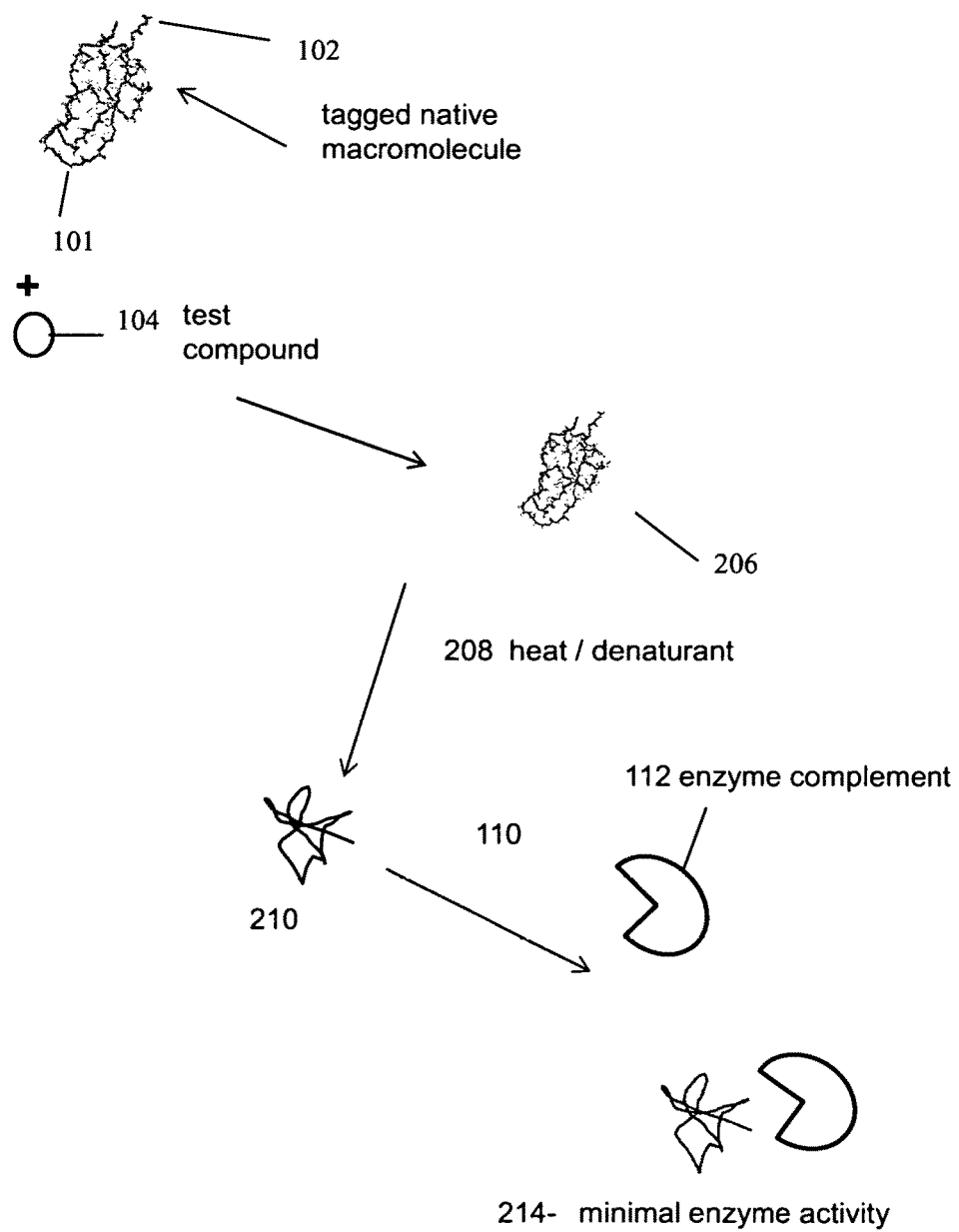
FIG. 2 is a schematic representation of the assay principle as in FIG. 1, except that in this situation the test compound does not bind to the tagged native macromolecule, resulting in denaturation of the tagged native macromolecule and further making the tag (labeling peptide) inaccessible for complementation.

The present methods may also be carried out with a series of heating pulses separated by cooling. The heat applied to the above described mixture of proteins and (potential) ligands serves, as described above to denature the protein; the resulting activity may be measured as shown in FIGS. 1 and 2. That is, the described methods may include a pulsed denaturation protocol where protein samples (+/−ligand) are subjected to several cycles (e.g. 10-200 cycles) of a short heat pulse at mild temperature which is followed by short re-equilibration at room temperature or below. These "pulse" protocols are easily carried out by using standard programmable thermal cycler instrumentation. This method avoids the need for high denaturation temperatures and long denaturation times and therefore increases the sensitivity of the method for detection of inhibitor binding. Given the present teachings, one may routinely determine optimal heating times, cooling times, cooling temperatures, and heating temperatures. These will be based on the biophysical properties of the target macromolecule under study, which include the temperature at which fifty percent of the molecules have unfolded (this temperature is known as the melting temperature or $T_m$). Other factors considered will be the expected affinity of the test compounds, the concentrations under study, etc.

General Method

Proteins, among other macromolecules, are one of the most studied and most targeted macromolecules in the pharmaceutical industry. A number of approaches have been designed and invented to study proteins, their structure, their chemistry, protein-protein interactions, protein-test compound interactions, and biological pathways where proteins participate, and to determine small molecule binding to proteins of interest. However, all these processes and measurements require proteins to be stable and active as proteins are susceptible to degradation or aggregation by a number of factors.

Macromolecules such as proteins denature when exposed to high temperatures, leading to their precipitation and aggregation. Binding of a compound to a macromolecule can increase its thermal stability and hence can be explored for a binding assay wherein one can measure a target macromolecule binding to a compound by measuring its thermal stability. Thus, a compound that binds at an active or allosteric site of a macromolecule such as a protein will form a complex and influence its thermal stability. This will lead to the compound being stable even at higher temperatures. As known, a thermal shift assay measures the thermal stability of a target protein and a subsequent increase in protein melting temperature upon binding of a ligand to the protein. A number of assays have been designed to study the thermal stability of proteins and investigate buffer conditions, ligands, co-factors, drugs and other compounds affecting this stability to identify protein complexes and further characterize them. An alternative format has also been disclosed to measure ligand binding to a target protein using a thermal shift assay. The assay works on both purified and non-purified protein samples even at a low concentration. However, the assay requires that denatured, precipitated proteins be removed by centrifugation and stabilized proteins be quantified by low dynamic range immune-assays such as Western blot or ELISA.

Thus, there is still a lack of a simple, sensitive, high throughput and precise readout assay to determine ligand binding in extracts, cells and tissues.

The present invention discloses a homogeneous binding assay to determine ligand macromolecule interactions, and further, how these interactions result in stabilization of the macromolecule. More specifically, the present invention discloses a homogeneous binding assay to determine ligand protein interactions, and further, how these interactions result in stabilization of the protein under heat stress.

Referring now to FIG. 1 and FIG. 2, a macromolecule 101 having a secondary or tertiary structure is linked chemically to a tag 102, which may be an enzyme fragment and may be a fusion protein with a protein macromolecule. A test compound 104 is mixed in a fluid environment with the tagged native macromolecule under buffer and physical conditions that will allow the test compound to bind to the native macromolecule in a specific recognition being evaluated. Non-specific binding is minimized by the buffer conditions. The buffer may contain low concentrations of detergent (0.05% Tween 20). Nonspecific binding is also minimized because of all the other proteins in the crude extract that discourage non-specific binding. The binding of interest is generally of specific high affinity binding. The test compound may be binding to a specific binding site designed in nature to receive and bind a ligand. During this incubation, the test compound is allowed to bind to the chimeric molecule comprising the target macromolecule linked to the labeling peptide, as shown at 106. As shown at arrow 108, the heat denaturation step is applied to the construct in the mixture. Then, as shown at arrow 110, a complementary enzyme fragment 112 is added to the mixture and will complement the tag 102 on macromolecules in which denaturation was minimized by the binding of the test compound. As shown at 114, an enzyme substrate or substrate mixture is added to the active enzyme found in the mixture, and a luminescent reaction is read using standard optical methods.

In FIG. 2, the corollary of the schematic of FIG. 1 is shown. Here, under similar conditions to those of FIG. 1, the test compound 104 does not bind to the macromolecule 101. The heat denaturation treatment in 208 causes the macromolecules in the mixture to form an aggregated mass 210. Aggregation increases with the degree of denaturation. Thus, when the enzyme fragment 112 is added at 110, no, or minimal active enzyme is produced, as indicated at step 214. The denaturation of a portion or all of the macromolecules effectively sequesters their tag 102, reducing the signal from the mixture.

The process of FIG. 1 and FIG. 2 may both occur at the same time in the same mixture and reaction. The degree of binding may be measured under different concentrations and/or in the absence or presence of binding inhibitors. In this case, the "test compound" may be a known binder, and the evaluation is that of a test inhibitor.

Macromolecules

The present invention provides an assay system for detecting macromolecule-ligand interactions following heat stress and denaturation, using EFC or fluorescent protein complementation. The macromolecule tested generally is a large molecule and is typically created by polymerization of smaller subunits (amino acids and nucleotides). Macromolecules of interest include polynucleic acids, proteins and carbohydrates, having defined three dimensional structures. The present macromolecules denature, i.e. lose their quaternary structure (sub units), tertiary structure and/or secondary structure by application of some external stress, such as an external compound, radiation or heat.

The target macromolecule may be a full length protein or a protein domain of interest to compound binding, such as by a small molecule agonist or antagonist of the target macromolecule. The target macromolecule is prepared in chimeric form by recombinant DNA methods. The chimeric protein may include a peptide label located at the amino or carboxy terminus of the target macromolecule. In addition, the target macromolecule may further be fused to an inactive exogenous polypeptide sequence that does not have any binding activity in the assay, but provides additional amino acid sequence (mass) for the target macromolecule to be partially denatured. For example, NF-κB DNA binding domain, described in Table 1 of U.S. Pat. No. 9,110,054 (SEQ ID NO: 5 in that document), entitled "Detectable nucleic acid tag," may be conveniently fused to the target macromolecule at a terminus opposite to the terminus containing the labeling peptide. The NF-κB binding amino acid sequence binds to specific DNA sequences, and is not known to bind to any small molecule drug candidates. Other inactive exogenous polypeptide sequences may be cloned into the target polypeptide and used, provided that they are known to not interact with the test compound, the labeling peptide, or the target macromolecule.

Labeling Peptide

A labeling peptide is attached to the target macromolecule which aids in the detection of macromolecule stability, compound binding to the macromolecule, inhibitors of compound macromolecule binding, and allosteric modulators, among other applications. A number of labeling moieties can be used to detect ligand macromolecule binding. β-lactamase-complementing reporter subunits as derived from β-lactamase can be constructed and utilized. Activity of the complementing β-lactamase can be detected using substrates for β-lactamase developed in the art which include a fluorescent donor moiety and a quencher, wherein the attached group is hydrolyzed off after the substrate enters the cell. Fluorescence energy transfer between the donor and quencher then can be monitored as an indicator of β-lactamase activity, as described in PCT WO 96/30540 published Oct. 3, 1996.

Green fluorescent protein (GFP): The protein is isolated from a marine organism and exhibits bright green fluorescence when exposed to light in the blue to UV range. GFP is tagged with a protein of interest, making a fusion protein which, upon binding to a compound that affects thermal stability of the protein, can then be measured using fluorescence microscopy.

A chromogenic peptide substrate can also be used wherein the enzymatic cleavage of the peptide p-nitro-aniline amide linkage in the chromogenic peptide substrate results in release of the chromophore p-nitroaniline. The reaction can be monitored spectrophotometrically.

Other labeling moieties include those in a ras-based recruitment system (RRS and SOS), a fusion-protein based system such as a yeast two hybrid system and the like. The labeling moiety can be coupled to the macromolecule of interest using any suitable method. The labeling moiety may be linked to the macromolecule of interest either directly or via a linker. Enzymes capable of catalyzing conversion of a substrate to a detectable reaction product, either directly or indirectly, such as beta-glucuronidase, alkaline phosphatase, peroxidase, luciferase and beta-galactosidase, may also be used as labeling moieties.

Beta-galactosidase (β-gal) is encoded by the E. Coli lacZ gene and can act as a labeling peptide. The enzyme activity can be monitored by different methods including live-cell flow cytometry and histochemical staining with a chromogenic substrate. The β-gal enzymes and its fragments (See U.S. Pat. No. 4,708,929) are required to have a number of characteristics. The fragments are substantially inactive individually, in that there is little, if any, background with only one fragment present in the presence of substrate. Secondly, the fragments have sufficient affinity for each other, that in the absence of other binding, e.g. by entities fused to the fragments, the fragments will combine to provide an active enzyme. The small fragment ("ED" or "PL") may be designed artificially and will not interfere with the biological activity of the gene or protein to which it is fused. The resulting fusion protein, as has been determined here, will fold properly and retain sites of activity, including enzyme activity, binding activity to other proteins, translocation capability, etc. The ED will usually be at least about 37, usually at least about 40 amino acids, and usually not more than about 110, more usually not more than about 90.

The β-galactosidase complementation system here is one that is made up of two or more β-galactosidase fragments or variants thereof. For example, in certain embodiments, the complementation system includes a first and second fragment of β-galactosidase (e.g., an α and ω fragment). In yet other embodiments, the complementation system may include more than two β-galactosidase fragments, such as a first, second and third β-galactosidase fragment (e.g., an α, β and ω fragment). In the present application, the small fragment of β-gal (also the signal producing peptide) will be referred to as the enzyme donor (ED). The signal producing peptide is one of a pair of fragments of an enzyme that is reconstituted when the two fragments, the enzyme donor ("ED") and the enzyme acceptor ("EA"), complex together. The ED will be a fragment of an enzyme that can be complemented with another fragment, the EA, to form an active enzyme. The ED fragment of the fusion protein will complex with the EA fragment owing to the affinity of the fragments for each other.

In other embodiments, the complementing fragments are high affinity fragments. High affinity components are generally two fragments of an enzyme with the fragments having sufficiently high affinity such that they can spontaneously bind to each other and reform a fully functional enzyme or enzyme subunit. Typically, at least 5% of enzymatic activity of the native enzyme is achieved when mixed under appropriate conditions in solution, sometimes about 10, 20, 30, 40, 50, 60, 70, 80, 90, 95, 99, or 100% of the enzymatic activity of the native enzyme. Determination of such activity can be performed using routine methods with the concentration at which the complemented enzyme and parental enzyme are compared typically being the same with a range of, e.g., between $10^{-3}$ to $10^{-6}$ M. High affinity components permit monitoring of the presence, absence, or increase of the complementing fragments as they form a complex with the interacting partner. For example, if one complementing fragment is present in the fusion protein (fused to the target macromolecule) and forms a complex with the test compound then the incubation with the second fragment after lysis of the cell will result in detectable enzymatic activity, thus permitting the analysis of cellular interactions. Accordingly, if the amount of high affinity components increases in the assay system, then the amount of detectable enzymatic activity will increase proportionally. Typically, large increases in the amount of activity are detectable up to a 1:1 reporter component ratio. See e.g., the experimental section below, as well as U.S. patent application Ser. No. 11/132,764 filed on May 18, 2005 for a review of such a rational approach as employed with an initial high affinity β-galactosidase complementation reporter system.

In a specific embodiment, the a peptide employed is one that complements the a peptide robustly in mammalian cells. The high affinity minimal a peptide permits sensitive, accurate analysis of cellular interaction events between various intracellular entities with only a minimum of interactions required for detection. Exemplary a peptides (enzyme donors) include

```
(Wild-type ED)
SEQ ID NO. 1:
MGVITDSLAVVLQRRDWENPGVTQLNRLAAHPPFASWRNSEE
ARTDRPSQQL (ProLabel™ enzyme donor, or "PL" ED)
SEQ ID NO. 2:
NSLAVVLQRRDWENPGVTQLNRLAAHPPFASWRNSEEARTDR,
and (modified ED, W34Y),
SEQ ID NO. 3:
MGVITDSLAVVLQRRDWENPGVTQLNRLAAHPPFASYRNSEE
ARTDRPSQQL.
```

A range of methods are available to measure the enzyme activity of β-galactosidase which include live cell flow cytometry and histochemical staining with the chromogenic substrate 5-bromo-4-chloro-3-indolyl β-D-galactopyranoside (X-Gal). See e.g., Nolan et al., Proc. Natl. Acad. Sci., USA, 85: 2603-2607 (1988); and Lojda, Z., Enzyme Histochemistry: A laboratory Manual, Springer, Berlin, (1979). Vital substrates for β-gal, which can be used in living cells, are also encompassed by the presently disclosed methods and materials. For example, a fluorogenic substrate, resorufin β-galactosidase bis-aminopropyl polyethylene glycol 1900 (RGPEG) has been described. Minden (1996) BioTechniques 20(1): 122-129. This compound can be delivered to cells by microinjection, electroporation or a variety of bulk-loading techniques. Once inside a cell, the substrate is unable to escape through the plasma membrane or by gap junctions. Another vital substrate that can be used in the practice of the presently disclosed methods and materials is fluorescein di-β-D-galactopyranoside (FDG), which is especially well-suited for analyses by fluorescence-activated cell sorting (FACS) and flow cytometry. Nolan et al., Proc. Natl. Acad. Sci, USA, 85:2603-2607 (1988) and Rotman et al. (1963) Proc. Natl. Acad. Sci, USA 50:1-6.

The active reconstituted β-galactosidase may also be detected using a chemiluminescence assay. For example, cells containing β-galactosidase fusions are lysed (with or without contacting with a crosslinking agent) in a mixture of buffers containing Galacton Plus substrate from a Galacto-light Plus assay kit (Tropix, Bedford Mass.). Bronstein et al, J. Biolumin. Chemilumin., 4:99-111 (1989). After addition of Light Emission Accelerator solution, luminescence is measured in a luminometer or a scintillation counter.

Fusion Protein

As disclosed in the present application, a macromolecule of interest is fused to a labeling peptide to form a fusion protein. A fusion protein includes a single continuous linear polymer of amino acids which includes the full or partial sequences of two or more macromolecules or two or more distinct proteins. Methods for the construction of fusion proteins are known in the art. A fusion protein gene construct may also include a single continuous linear polymer of nucleotides which encodes the full or partial sequences of two or more distinct proteins in the same uninterrupted reading frame. Further, the fusion gene construct of the invention is introduced into the cells to assay for ligand binding following denaturation. The fusion gene construct may be introduced into cells by any method of nucleic acid transfer known in the art. Different fusion gene constructs encoding unique fusion proteins may be present on separate nucleic acid molecules or on the same nucleic acid molecule.

The fusion protein may also comprise a target macromolecule fused to a β-gal fragment as a labeling peptide. Thus, in some embodiments, the fusion protein as used in the present assay comprises a protein of interest and a labeling peptide, which, after treatment, is contacted with a second label (enzyme fragment, antibody, etc.) to generate a signal.

Use of a Protein as a Target Macromolecule (Target Protein)

The protein used as a target macromolecule can be any conceivable polypeptide or protein that may be of interest, such as to study or otherwise characterize. Proteins of interest may include transferase, oxidoreductase, hydrolase, ligase, and isomerase, along with kinases, phosphatases, carboxylases, phosphodiesterases, dehydrogenases, oxidases, peroxidases, proteases, signaling proteins, metalloproteins, cytoplasmic proteins and nuclear localization proteins. The target protein may be obtained from any source such as a natural occurring source, e.g., cells, tissues, biological fluids, tissue biopsies, soil, water, etc.

The bromodomain protein family is the family described in the SCOP database, scop.mrc-lmb.cam.ac.uk/scop-1.75/dataiscop.b.b.ec.b.b.html. Of particular interest is the BET family of bromodomain proteins, e.g. BRD1-BRD4 and related proteins, as described at Filippakopoulos et al., "Selective inhibition of BET bromodomains," Nature 468: 1067-1073 (23 Dec. 2010).

Target proteins may also include cell membrane proteins, defined as proteins that interact with biological membranes and comprise integral membrane proteins and peripheral membrane proteins. Target proteins may also include signaling proteins that govern basic cellular activities and coordinate cell actions.

Engineered Cells

The present invention contemplates the use of a cell engineered to carry a transgene expressing (or over expressing) a fusion protein of a target macromolecule and a labeling peptide as described herein. The labelling peptide may be a PL at the C terminus of the protein of interest.

The host cells used in the examples here are HEK293 (human embryonic kidney cells). This cell line may be obtained from the ATCC and other vendors. Methods for engineering HLK cells to express transgenes are known. For example, see Doering et al., "Directed Engineering of a High-expression Chimeric Transgene as a Strategy for Gene Therapy of Hemophilia A," Mol Ther. 2009 July; 17(7): 1145-1154 and US 20130344537, "Mammalian expression vectors and uses thereof," published Dec. 26, 2013 for details on creation of the cells that can be used here.

Other cells can be engineered for use in the present methods. These include CHO (Chinese hamster Ovary cells), BHK (baby hamster kidney cells), NSO (mouse myeloma cells), SP2/0 (ATCC CRL-1581), etc. Suitably engineered cells, containing a PL tag are commercially available from DiscoveRx Corporation, Fremont, Calif.

Kits

Also provided by the subject invention are kits for use in practicing one or more of the above described applications. In certain embodiments, kits at least include a cell that expresses, either constitutively or inducibly, a fusion protein that includes a protein of interest and a β-galactosidase fragment, as reviewed above. In certain embodiments, kits include elements for making such cells, e.g., nucleic acids encoding a fusion protein present on vectors and/or nucleic acids encoding a β-galactosidase fragment to which proteins of interest can be fused using standard molecular biology techniques, as reviewed above. The kits may further include one or more additional components which find use in practicing certain embodiments of the invention, including but not limited to enzyme substrates, cell growth media, etc.

In certain embodiments, the kit may include (a) a cell comprising an expression vector for expressing a fusion protein comprising a protein of interest fused to an ED (enzyme donor) fragment of β-galactosidase (component I), (b) an EA (enzyme acceptor) fragment of β-galactosidase (component II) for adding to a cell after it has been incubated with a test compound and (c) a β-galactosidase substrate (component III) for detecting binding of the EA to the ED in the fusion protein, and, optionally, a lysis buffer for lysing cells prior to or during addition of the EA. Lysing the cell facilitates contact of the labeling peptide (ED) with the EA. The kit may further comprise an expression vector containing multiple cloning sites permitting the user to insert a selected protein of interest. The kit may further comprise an expression vector for expressing a fusion protein that contains exogenous sequence fused to an inserted target protein. The exogenous sequence may encode any protein known not to interact in the assay, such as, for example, a plant or non-mammalian virus protein.

The kit may further contain positive and negative controls relevant to the protein of interest.

In addition to the above components, the subject kits may further include instructions for practicing the subject methods and intact cells for use with the in-cell embodiments. These instructions may be present in the subject kit in a variety of forms, one or more of which may be present in the kit. One form in which these instructions may be present is as printed information on a suitable medium or substrate, e.g., a piece or pieces of paper on which the information is printed, in the packaging of the kit, in a package insert etc. Yet another means would be a computer readable medium, e.g., diskette, CD, etc., on which the information has been recorded. Yet another means that may be present is a website address which may be used via the internet to access the information at a removed site. Any convenient means may be present in the kits.

EXAMPLES

Figure 3:
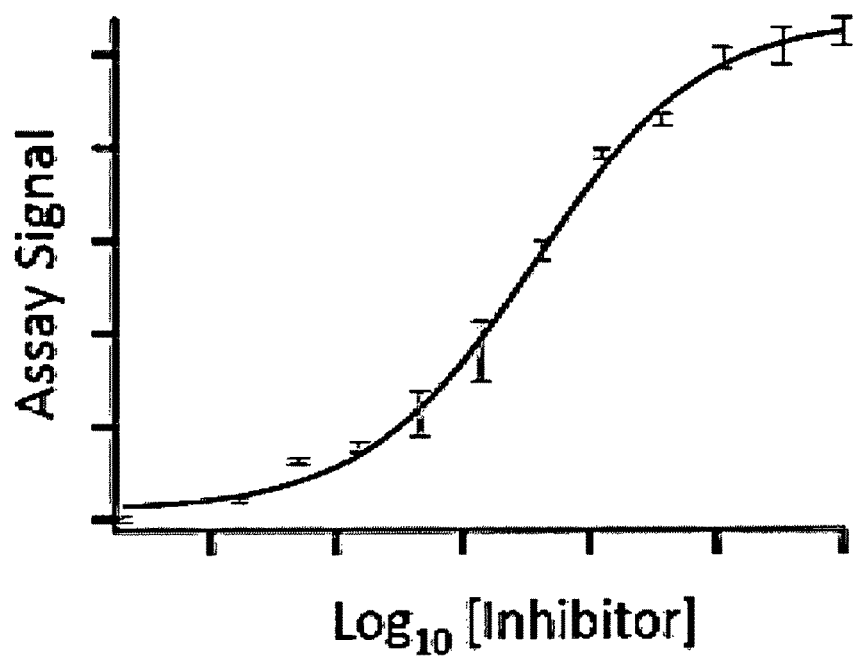
FIG. 3 shows a graph of a fusion protein of BRD4 (1) -ProLabel™ enzyme donor (ED) in a crude cell extract incubated with an indicator (substrate) and then heated at about 45° C. for 30 seconds. An inhibitor that binds to the BRD4 (1) is added at different concentrations between 0 and 100 uM. It can be seen that a dose-response protection of the fusion/BRD4(1) is achieved by binding of the inhibitor. In all of the Figures illustrating BRD4(1), the construct used is NFκB DNA Binding Domain—Linker-BRD/1(1)—Linker ED. The NFκB DNA binding domain sequence in the fusion protein does not play an active role in these examples.
Figure 4:
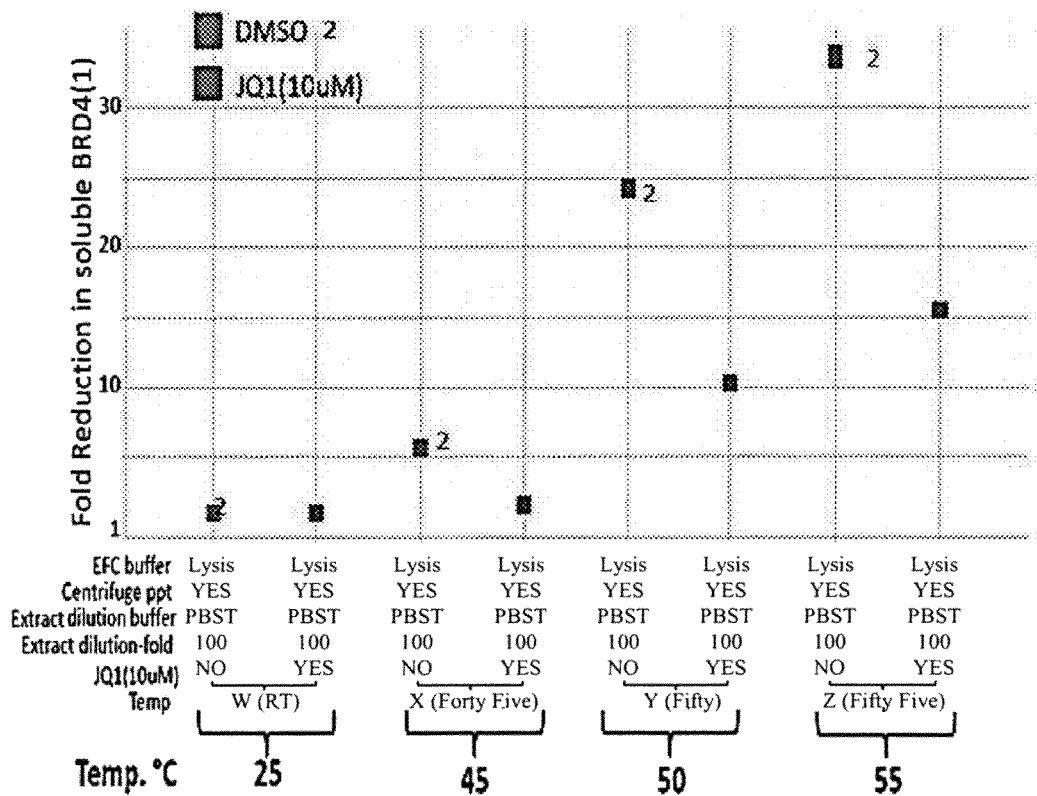
FIG. 4 is a plot comparing a non-inhibitor DMSO (labeled "2") with JQ1, (6S)-4-(4-Chlorophenyl)-2,3,9-trimethyl-6H-thieno[3,2-f][1,2,4]triazolo[4,3-a][1,4]diazepine-6-acetic acid, 1,1-dimethylethyl ester, known to be a selective BET bromodomain inhibitor. As can be seen, the enzyme complementation ability of the BRD4(1) is reduced by a significant amount at temperatures between 45 and 55° C., while the presence of JQ1 at 10 uM protects BRD4(1) from denaturation and enzyme complementation is reduced to a much lesser extent.
Figure 5:
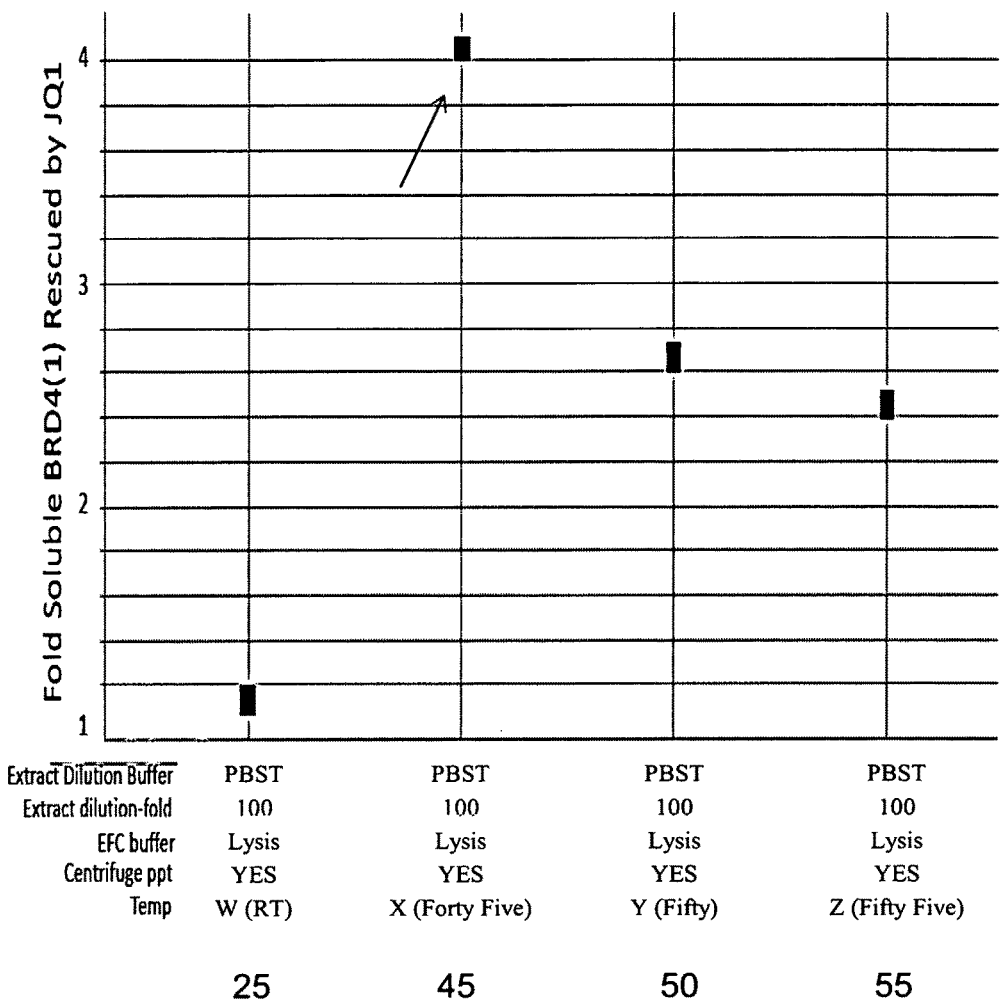
FIG. 5 is a plot that also shows protection of BRD4(1) at 45, 50 and 55° C. in the presence or absence of JQ1 binding to the BRD4(1). As shown at the arrow, the protection from heat denaturation at 45° C. is more significant than at 25, 50, or 55° C. The incubation at 25° C. was run as a control, not to indicate thermal denaturation.

The present working examples demonstrate that the thermal denaturation of a BRD4(1)-ED fusion can be measured in a facile, sensitive, and precise manner by using enzyme fragment complementation (EFC) (FIGS. 4 and 5). Furthermore, the observed denaturation can be rescued by the presence of small molecule BRD4(1) inhibitors in a dose-dependent manner (FIGS. 3-7). The method is homogeneous and does not require wash steps or centrifugation (FIG. 6) and is thus amenable to high throughput applications; and the resultant data have high precision (FIGS. 3 and 7). The method can be used to distinguish molecules with different potencies for BRD4(1) as well (FIG. 7).

Example 1: Measuring Binding of BRD4(1) ED Fusion Protein with a Known Ligand (JQ1)

The present experiment was done to study binding of a ligand to BRD4(1) fusion protein under heat stress and if the ligand binding protects the fusion protein from denaturation.

To carry out the assay, a fusion protein [BRD4(1)-ED], which also contains an NFκB DNA binding domain at the N-terminus, was constructed with BRD4(1) and a ProLabel™ enzyme donor (ED) fragment. The fusion protein in crude cell extract was incubated with a known potent inhibitor (JQ1) in a concentration ranging from 0-100 micromolar. The incubation was for 1 hour at room temperature. The samples were then heated to 45° C. for 30s. EA was subsequently added into the samples (along with luminescent substrate for beta-galactosidase) and complementation was measured by measuring luminescence. As shown in FIG. 3, binding of the inhibitor to BRD4(1) fusion protein and binding could rescue the fusion protein from denaturation in a dose-dependent manner. Exquisite precision was obtained for duplicate samples.

Example 2: Measuring Thermal Denaturation of BRD4(1) in the Presence and Absence of JQ1

The present experiment was done to study denaturation/aggregation of BRD4(1) in the presence and absence of an inhibitor. The inhibitor as used in the present experiment is JQ1.

To carry out the assays, two separate samples were prepared wherein one sample comprises BRD4(1)(fusion) and no inhibitor whereas another sample comprises BRD4(1)(fusion) and an inhibitor. The inhibitor as used in the present experiment is JQ1 and was used at a concentration of 10 micromolar. Following incubation, samples were exposed to increased temperatures (25° C., 45° C., 50° C. and 55° C. respectively). The samples were then centrifuged to separate the precipitate. As can be seen from FIG. 4, JQ1 bound to the fusion protects BRD4(1) from denaturation as compared to BRD4(1) with no inhibitor binding.

Example 3: Measuring Denaturation of BRD4(1) Fusion Protein in the Presence of JQ1

The present experiment was done to study how binding of JQ1 protects BRD4(1) fusion protein from temperature induced denaturation.

To carry out the experiment, a fusion protein was constructed comprising NFκB-BRD4(1)-ED. The fusion protein from cell lysate was incubated with JQ1 (10 μM). The samples were then exposed to several temperatures (25° C., 45° C., 50° C. and 55° C. respectively). As can be seen from FIG. 5, fold soluble BRD4(1) was maximally rescued at 45° C., and proteins slowly started retaining the denatured state at higher temperatures.

Example 4: The Effect of Centrifugation on the Assay Readout

The present experiment was done to study the importance of centrifugation to separate denatured fusion protein in a composition also containing soluble, bound fusion protein, and how it affects the final readout.

To carry out the experiment, a fusion protein was constructed comprising NFκB-BRD4(1)-ProLabel™ enzyme donor(ED). The fusion protein was then incubated with a ligand and the luminescent readout was done in the presence of a detergent-containing cell lysis and in PBS. The samples were then kept at room temperature or exposed to 45° C. elevated temperature. Each sample was divided into 2 wherein one part was centrifuged and other part of the sample was not centrifuged.

Figure 6:
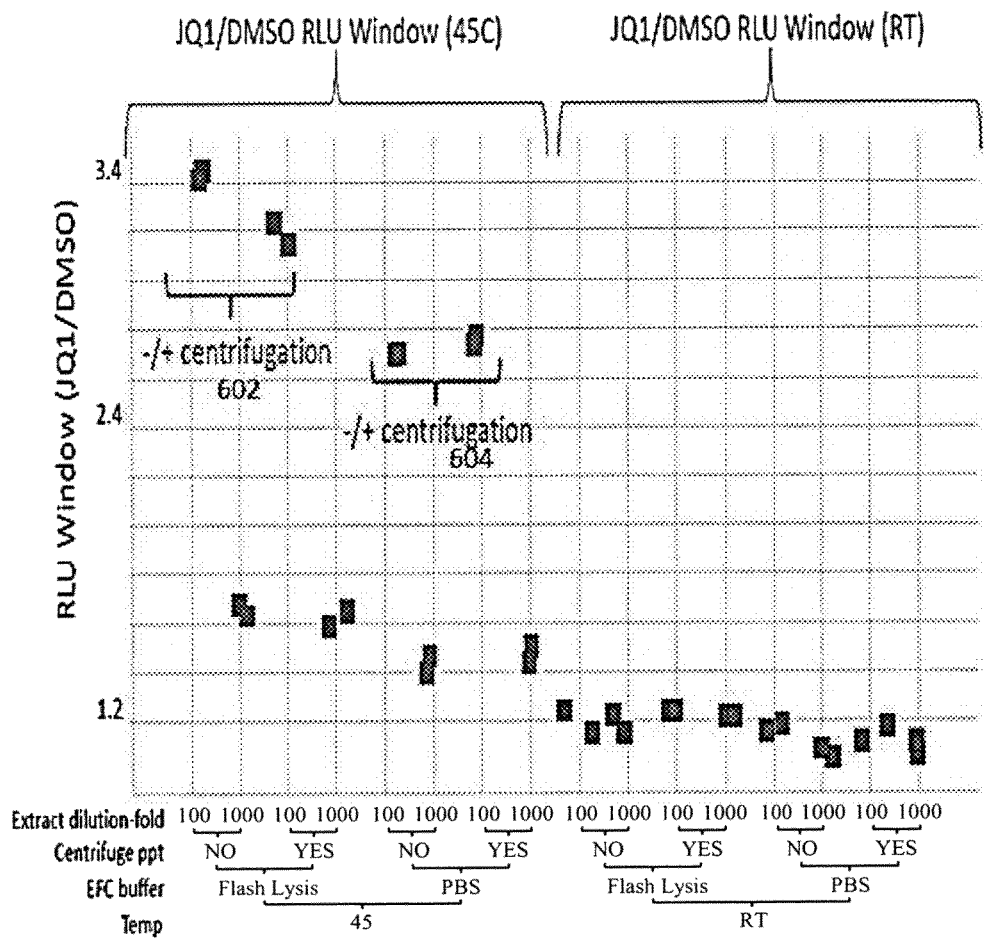
FIG. 6 is a plot of the RLU (relative luminescence units) showing that little difference is seen whether or not centrifugation is carried out, as shown by the closely spaced spots at 602 and 604.
Figure 7:
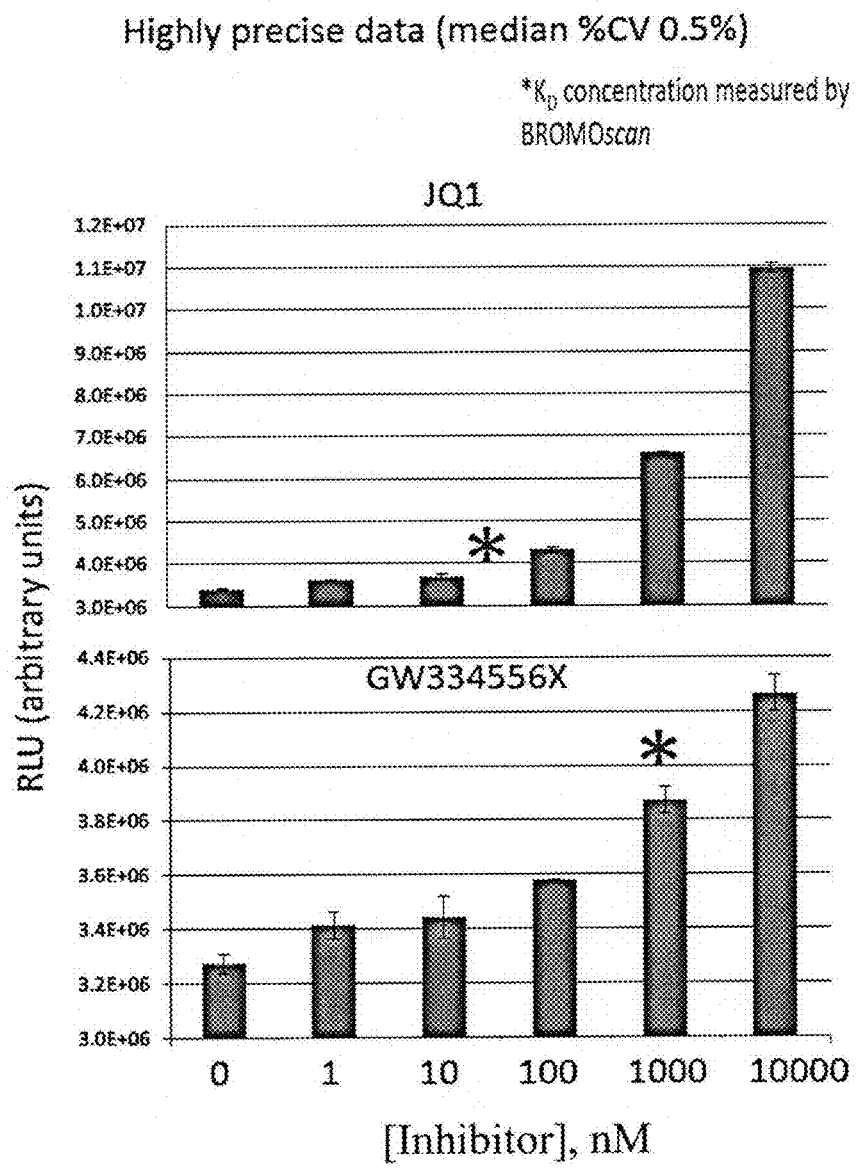
FIG. 7 is a pair of bar graphs showing dose response relationships in the ligand binding assay with potent BRD4 (1) inhibitor JQ1 (top figure) and a known, less potent BRD4(1) inhibitor GW334556X (bottom figure). BRD4(1)-ProLabel™ enzyme donor (ED) fusion protein in a crude cell extract was incubated with an indicator and heated to a target temperature in a PCR thermal cycler machine. The asterisks indicate the $K_D$ (dissociation constant) concentration as measured by the BROMOscan® Technology Platform available from DiscoveRx Corp. This shows that the present assay can determine dose-response relationships. The coefficient of variance observed here was less than 1%. The assay is also very reproducible. GW334556X is further described in Chung et al. J. Med. Chem. (2012) 55: 576.

As can be seen from FIG. 6, there is little difference in the assay readout whether the sample was centrifuged to separate the precipitate or not. Therefore, the experiment shows that centrifugation is not required in the present assay and the ligand binding can be assayed using EFC in the crude cell extract without a physical separation step.

Example 5: Dose-Response Curves for Known BRD4(1) Inhibitors Following Ligand Binding Assay The present experiment was done to determine the dose-dependence of ligand protein binding following the ligand binding assay as described in the present application.

To carry out the assay, a fusion protein was constructed as described above. The fusion protein was then incubated with a ligand (JQ1 and GW334556X) respectively, as shown in FIG. 7. The incubation at the indicated concentrations was at room temperature for 1 hour with 1:100 diluted extract (about 10 nM BRD4(1) concentration). The samples were then heated to 45° C. for 3 minutes followed by adding EA and a luminescent beta-galactosidase substrate (Flash Substrate) to measure complementation. The error bars indicate 3X standard deviation (99.7% confidence interval). Interactions were detected with high statistical significance when compounds were screened at ≥3X the $K_D$ concentration.

Inhibitor $K_D$ values measured by another method (BROMOscan® assay panel) are indicated by * (align * to x-axis concentration value). The BROMOscan® assay panel has been developed by DiscoveRx Corporation, Fremont, Calif. The BROMOscan® platform measures the interactions between test compounds and a panel of bromodomain assays. See more at: discoverx.com/technologies-platforms/competitive-binding-technology/bromoscan-technology-platform#sthash.ZjaxX6mR.dpuf.

Example 6: Comparison Between a Standard Denaturation Protocol and a Pulse Denaturation Protocol The methods of Examples 1-5 can be implemented by a number of heating steps. The following examples pertain to a protocol in which the macromolecules (e.g. proteins) are heated at a temperature that does not, in a single heating step, cause significant denaturation (melting) but that, in a series of heating steps, does. The steps are applied such that one heating step, which is not effective to melt the protein, is followed by a series of heating steps that, cumulatively, do cause denaturation (in the absence of a ligand). For accomplishing this, a thermoelectric heating and cooling device may be employed and preprogrammed to carry out predefined heating and cooling (non-heating) steps. The preferred thermoelectric heating and cooling device is based on a Peltier Junction. These devices can carry out active heating and cooling; alternatively, the present devices may be provided with a large heat sink. Details of Peltier heating and cooling of substrates and masks may be found at U.S. Pat. No. 3,161,542. The methods described below may comprise a number of heating steps, separated by cooling steps, and a series of one or more heating temperatures. These numbers can be determined using the teachings herein. The method may be carried out with a heating step based on the properties of the macromolecule that is the binding target. Once a temperature T and a time t are determined, T may be reduced in increments, preferably below the melting temperature of the macromolecule, and the time t can be subdivided into a series of heating steps whose total, at least initially, is total time. Cooling steps may be based on the equipment used to return the reaction mixture to ambient or near ambient temperature (~25° C.). Possible, non-limiting, combinations are 10-70 pulses at 3/–50° C. for 5-10 seconds, with a 15 second to 2 minute cooling interval. Other examples are given below. The volume of the reaction mixture should also be considered, where larger volumes suggest the use of more and longer pulses.

Figure 8A:
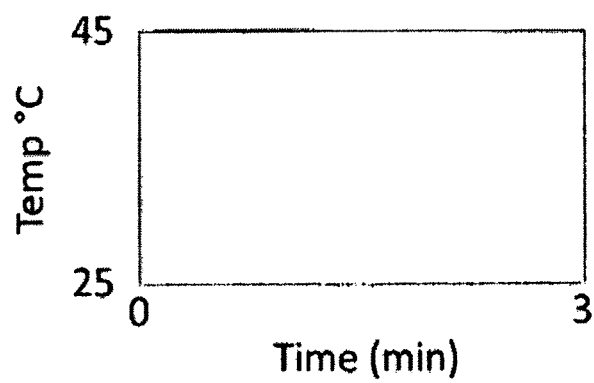
FIG. 8A, 8B is pair of graphs showing an example of a pulse-denaturation protocol.
Figure 8B:
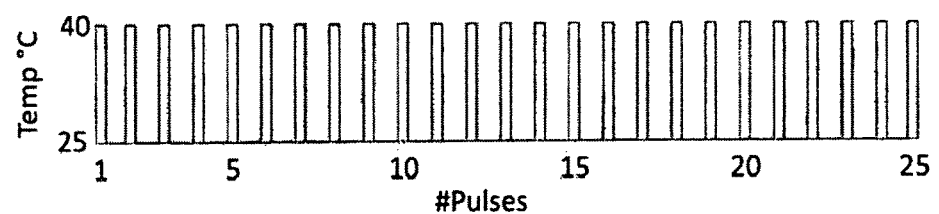

As shown in FIG. 8A, a standard denaturation profile comprises a single cycle of a high temperature pulse followed by an extended denaturation time for protein denaturation. A pulse denaturation profile, in contrast, comprises several cycles of a heat pulse at a mild temperature which is followed by a brief denaturation and a resetting to a lower temperature (FIG. 8B). The temperatures in FIGS. 8A and 8B represent heat settings. The temperature in the mixture will, as is known, follow a curve. The cooling steps in FIG. 8B will result in a ramp up of the mixture over time, according to the embodiment. That is, the existing temperature of the mixture during a cooling step remains greater than a temperature in the mixture that may be existent and measured during a previous cooling step.

The temperature for a standard denaturation protocol may be 45° C. or higher whereas the temperature for a pulsed denaturation may be 40° C. or lower than 40° C. Denaturation of macromolecules runs in minutes in a standard denaturation protocol whereas in a pulse denaturation protocol there is a brief denaturation step running in seconds followed by reduction of the temperature to room temperature or even lower before the next heat pulse.

Example 7: Mathematical Modeling Studies

Figure 9:
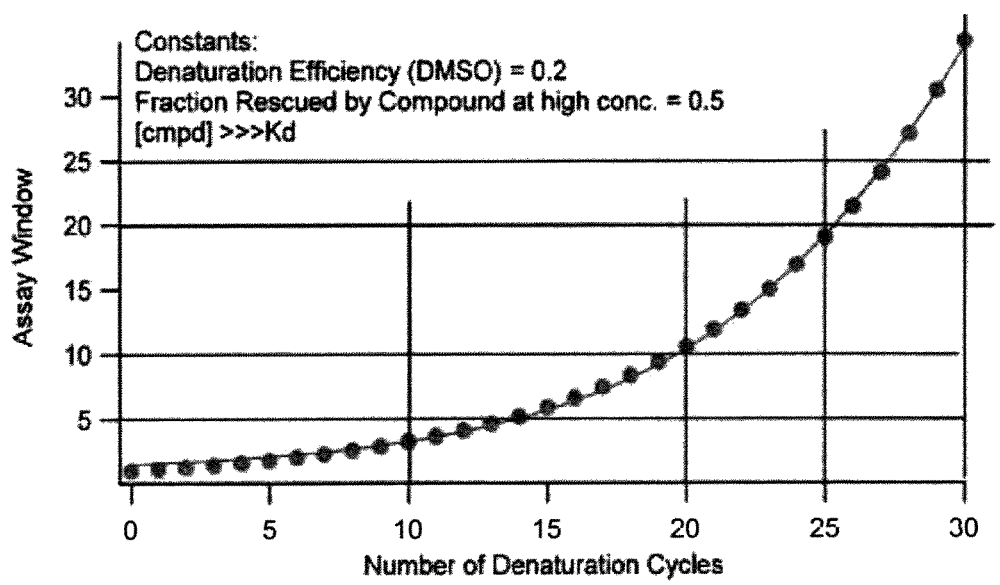
FIG. 9 is a graph showing a mathematical model calculating an assay window versus the number of denaturation cycles. It shows that the assay window grows exponentially with cycle number. "Assay window" is defined as luminescence signal in the presence of known ligand divided by luminescence signal in the absence of known ligand after x cycles. The model assumes that a low fraction of folded protein denatures each cycle and cannot refold/reactivate on subsequent cycles. The model assumes that, in each cycle, the known ligand rescues 50% of the protein from denaturation. The model also assumes that compound binding returns to room temperature levels each cycle during temperature shift from set point to room temp. The degree to which compound binding protects the protein from denaturation and the total amount of denaturation for the no compound control denaturation/naturation indicates the assay window. An assay window may be estimated from data presented here by comparing the base line signal (RLU) to the maximum signal in a given experiment.

FIG. 9 shows results of a mathematical modeling showing advantages of pulse denaturation. The Y axis on the graph shows an assay window which is defined as luminescence signal in the presence of known ligand divided by luminescence signal in the absence of known ligand after X no. of cycle. The X axis on the graph shows the number of denaturation cycles wherein the denaturation is done by pulse heating.

The model is based on an assumption that a low fraction of folded protein denatures during each cycle and cannot refold or reactivate on subsequent cycles, while incubating the protein with a known ligand rescues half or more than half of the protein from denaturation. The protein ligand binding level returns to room temperature or below level during each cycle when the temperature is brought down to room temperature or lower.

The mathematical modeling graph shows that multiple cycles of gentle denaturation are expected to produce a robust assay window even though the denaturation temperature is below the melting temperature.

Figure 10:
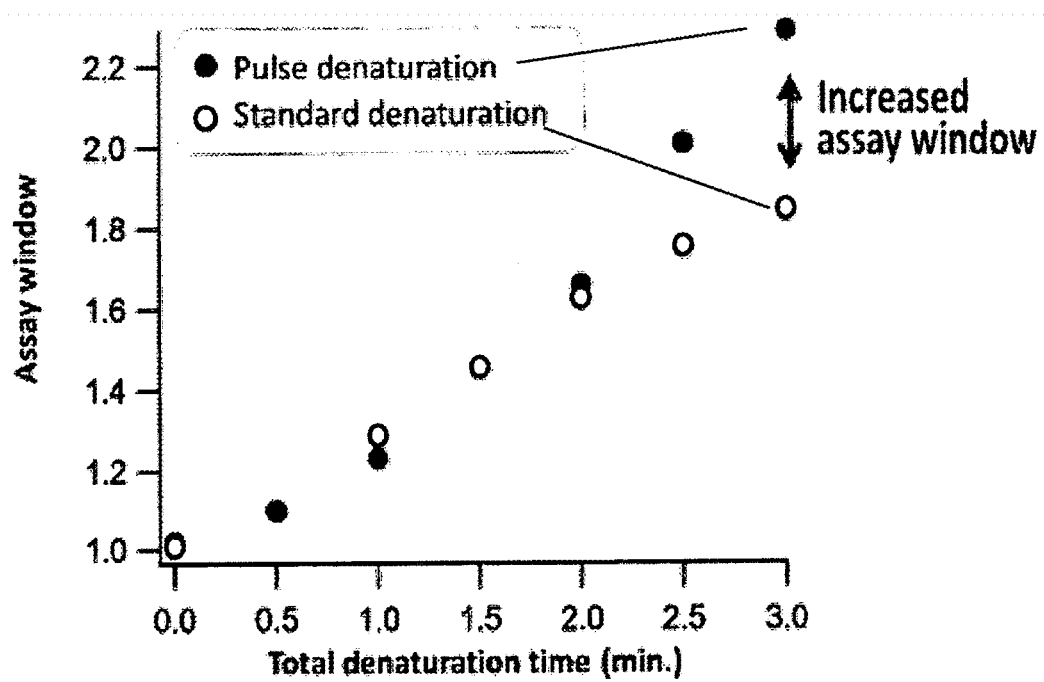
FIG. 10 is a graph comparing a "standard" (constant heat) protocol with a pulse protocol. The assay window for the pulse denaturation is shown in black circles. The pulse system results, over time, in an increased assay window in comparison to the standard denaturation, which is shown in white circles. Thermal melting assay windows for both "standard" and "pulse" protocols were measured for the BRD9-Bromosporine interaction. Bromosporine is N-[(6-3-Methanesulfonamido-4-methylphenyl)-3-methyl-[1,2,4]triazolo[4,3-b]pyridazin-8-yl]carbamate, commercially available from Tocris Biosciences.

Example 8: Study of BRD9-Bromosporine Binding Using Standard and Pulsed Denaturation Protocols FIG. 10 shows a dose response curve for BRD9-bromosporine binding following standard and pulsed denaturation protocols. Cell extracts containing the ED tagged BRD9 were diluted in PBST and incubated for 1 hour at room temp. with 25 uM Bromosporine or with 0.1% DMSO/0.9% MEG (49.5 ul cell extract+0.5 ul 2.5 mM Bromosporine or 0.5 ul 10% DMSO/90% MEG). The samples were then subjected to heat denaturation at 45° C. either with the pulse method or with the standard (one step) denaturation protocol. In the first case the samples were repeatedly exposed to 45° C. for 0.5 min (with a 1 minute interval at room temperature between heat pulses) to a total heating time between 0.5 to 3 minutes ("Pulse denaturation", dark circles). In the second case the samples were heated up for the same total amounts of time (0.5 min to 3 minutes) but in a single step ("standard denaturation", white circles).

Soluble protein was then quantified by EFC (heat denaturation renders the ED inaccessible for complementation to EA). EFC reactions were set up as follows: 5 ul cell extract was incubated for 30 min with 10 ul EA, 10 ul EA Dilution Buffer, 20 ul Flash lysis buffer, 20 ul Flash Substrate, and 135 ul PBS. Assay windows were calculated by dividing the RLU signal of the protein with bromosporine by the RLU of the protein with DMSO/MEG.

As can be seen from the curve, the assay window improved with pulse denaturation (6 repetitive pulses, with a total of 3 minutes of heating) giving improved binding assay results without extended heating.

Example 9: Study of CREBBP/SGC-CBP-30 Binding Using Standard and Pulsed Denaturation Protocols FIG. 11 shows a dose response curve for CREBBP/SGC-CBP-30 binding following standard and pulsed denaturation protocols. (CREBBP is CREB binding protein having the official symbol CREBBP; SGC-CBP-30 is a small molecule that is a selective inhibitor of CREBBP, having IUPAC name (S)-4-(1-(2-(3-chloro-4-methoxyphenethyl)-5-(3,5-dimethylisoxazol-4-yl)-1H-benzo[d]imidazol-1-yl)propan-2-yl)morpholine. Cell extracts containing ED tagged CREBBP and also fused to the DNA binding domain of NFκB were incubated for 1 hour at room temperature with serial dilutions of SGC-CBP30 (49.5 ul cell extract diluted in PBST+ 0.5 ul of 100X compound in 10% DMSO/90% MEG) and then heat denatured in the conditions indicated on the graph. Soluble protein was quantified by EFC with the same protocol used for BRD9. Data were fitted with the Hill Equation and $EC_{50}$s were calculated. FIG. 11 shows that the pulse denaturation shows a higher signal gain at a lower concentration of inhibitor and still shows a dose response curve over the entire range between minimum and maximum detectible concentrations; therefore the sensitivity of the assay using pulse denaturation is improved over the sensitivity of the assay using a standard denaturation method. The addition of a second polypeptide (NFκB) increases the assay window for this target protein (CREBBP).

Example 10: Study of ABL1 Binding to a Range of Small Molecule Inhibitors Using Pulsed Denaturation FIG. 12 shows pulse denaturation technology applied to a protein kinase (ABL1) to test a range of small molecule inhibitors known from the literature to bind this target with a wide range of affinities. $EC_{50}$ dose response curves for the seven inhibitors shown on the graph (inhibitor name labels and corresponding curves are in the same left to right order) were measured against ED-tagged ABL1. The overall procedure used was similar to that described for Example 9 and used a pulse denaturation sequence of 30 cycles of: 7 seconds at 42° C. followed by 60 seconds at 25° C. The affinity of the inhibitors for ABL1 decreases from left to right on the graph; the leftmost curve identifies the inhibitor of highest affinity and the rightmost curve identifies the one of lowest affinity. Ordered from higher to lower affinity, the inhibitors are dasatinib, ponatinib, imatinib, VX-680, staurosporine, SU-14813, and purvalanol B. The potency rank order for these seven inhibitors is in good agreement with published values (Davis et al. Nat Biotechnol. 2011 Oct. 30; 29(11):1046-51. doi: 10.1038/nbt.1990.).

At each concentration, the inhibitors can be compared as to their degree of binding to ABL1. At an inhibitor concentration of 1 nM, for example, a maximal signal is seen for dasatinib but a minimal signal is seen for staurosporine. This means that at this concentration, dasatinib protects ABL1 against denaturation to a much greater degree than staurosporine does, a result that reflects the higher affinity of dasatinib for ABL1.

Example 11: Study of Methyltransferase G9a/UNC-0638 Binding Using a Standard Denaturation Protocol FIG. 13 shows a denaturation protocol applied to a protein methyltransferase (G9a) to test the known inhibitor UNC-0638 in a dose response curve. UNC-0638 was tested against ED-tagged G9a (with NFκB inactive exogenous polypeptide sequence), and the overall procedure used was similar to that described for Example 9. This proof of concept G9a study was performed using a single denaturation step of 3 minutes at 50° C. The increase in the assay signal starting at about $10^2$ nM and continuing through $10^4$ nM shows that the protection against denaturation of G9a increases in a dose-dependent manner with the concentration of the inhibitor. The protection results from inhibitor binding, the associated $EC_{50}$ value of which may be derived from the curve. This example, along with the other examples disclosed herein, shows that the assay may be used to measure binding of compounds to a wide variety of macromolecules.

This example shows that a single heat pulse at 50° C. for 3 minutes yields a useful assay with a methyltransferase enzyme and indicates the broad applicability of the method. One may refer to the comparison between the present "standard," or single pulse, protocol and a multi-pulse protocol and expect that the present assay window would be improved by a pulse protocol.

Example 12: Kit for Measuring Inhibitors of BRD4(1)

The exemplary kit is prepared as a 96-well plate format kit for the in vitro biochemical assessment of BRD4(1) inhibitor potency. The assay uses enzyme fragment complementation (EFC) and pulse denaturation technologies to measure ligand-dependent thermal stabilization of target proteins. This approach enables the measurement of quantitative inhibitor apparent $EC_{50}$ values. The kit provides sufficient reagents to perform four 96-well plate experiments (16×12 point dose-response curves in duplicate) and is optimized for the measurement of inhibitor $EC_{50}$ values. The streamlined and rapid assay protocol does not require cumbersome sample processing, plate transfer, or centrifugation steps. The assay provided in this kit is not optimized for single concentration screens of compound collections. The kit may be used to validate screening hits identified by related or orthogonal methods; monitor compound potency improvements during lead optimization; obtain rapid results (less than 4 hours start to finish), with less than 60 minutes of hands-on time; and measure inhibitor $EC_{50}$ values over a broad potency range (high picomolar to millimolar). The kit includes a fusion of the protein of interest with a beta galactosidase enzyme fragment ("PL"); a positive control, dilution buffer and two enzyme substrate reagents—β galactosidase fragment complementing PL; and β galactoside substrate.

Step 1 of the exemplary kit instructions is to prepare the test and control compounds in serial dilutions. One prepares a series of dilutions. Then the BRD4-PL reagent is added and the mixture is incubated. Step 2 is to set up a compound binding reaction. Step 3 is instructions for a pulse denaturation protocol. The pulse denaturation protocol is summarized as follows: a. Transfer PCR plate to a thermocycler and perform 40 pulse denaturation cycles. One denaturation cycle is defined as: 7 seconds at 40° C. followed by 60 seconds at 25° C. b. After the cycling program is complete, the plate can be read-out by EFC immediately or stored at −80° C. if the readout is to be performed at a later time. The thermocycler's heated lid is ideally set to 40° C., but some instruments have a default setting of 95° C., which is also acceptable. Step 4 of the instructions describes the EFC detection protocol in each well of the assay plate. Step 5 comprises instructions for reading the samples on a luminescence plate reader at 1 second/well and data analysis which will show a dose response of the compound(s) tested.

The following examples describe use of an in-cell method (InCELL Pulse™ method) as described above. In general, the examples use a target macromolecule (protein or protein domain or portion) that is linked to labeling peptide, here the β-galactosidase enzyme fragment termed ProLabel™ enzyme donor. These fusion proteins are subjected to denaturation while still in the cell where they have been expressed. The vectors for expressing the fusion proteins in the cell to be treated e.g. heated) can be prepared by conventional recombinant methods, described, e.g. in Horecka at al., "Analysis of intracellular modifications," US20060019285, published 26 Jan. 2006, which is also, as noted at the last paragraph here. The chimeric molecule may be prepared in any convenient cell. Preferably, the same cell is used for partial denaturation in the assay, and is a mammalian cell. The following examples use the following protocol:

Day 1: Transfect HEK293 cells with vector expressing ProLabel™-tagged target protein
Day 2 (all following steps): Detach transfected cells using Accutase® cell detachment solution, count, and dilute to 100,000 cells/ml
Add 1 uL of a 50× compound stock or DMSO ctrl to each well of black per PCR plate
To each plate with comound/DMSO add 50 µl of cell suspension (5,000 cells)
Incubate at 37° C. (e.g. for 4 hours)
Using thermocycler, perform denaturation step on cells in plate (e.g. 3 minutes at 45° C.)
Add 60 µl EFC reagents (EA, cell lysis buffer, and substrate, i.e. chemiluminescent betaglactosidase substrate), incubate at room temp. for 30 min
Read out well signals using luminometer

Example 13: In-Cell Method Using a Kinase and its Inhibitor: FIG. 15

Assay Metrics (n=3)
"n=3" means that the experiments were performed in triplicate. The values shown are +/−one standard deviation.

| Inhibitor | $EC_{50}$ (nM) | Assay Window |
|---|---|---|
| Dasatinib | 2.8 +/− 0.5 | 5.2 +/− 0.38 |
| VX-680 | 570 +/− 230 | 3.6 +/− 0.058 |

Published dasatinib cell potency against ABL1-driven cells: $IC_{50}$=1 nM
Blood. 2006; 108(7):2332-2338. Assay uses ABL1 kinase domain expressed with a C=terminal PL tag (SEQ ID NO: 2).
Assay Protocol
ABL1 assay is performed essentially as follows:
1. Discard growth medium from 10 cm plate with HEK293 cells transfected with plasmid expressing ABL1-PL fusion and rinse cells with PBS. 2. Detach cells with 1 ml Accutase® cell detachment solution. 3. Dilute cells with 10 ml 1X DMEM 1% FBS medium. 4. Count cells. 5. Dilute cells to 100,000 cells/ml in 1×DMEM 1% FBS medium, using appropriate volumes for cell count. 6. Dispense 1 ul serial dilution of compound. 7. Add 50 ul cells. 8. Incubate at 37° C. for 5 hrs. 9. Perform pulse denaturation in 96-well black PCR plates from Thermo Scientific (Prod. No. AB-0800/K) using a standard PCR thermocycler (MJ Research DNA Engine) according to the following set of conditions:

| Pulse temp. (° C.) | Pulse time (sec.) |
|---|---|
| control | No pulse |
| 48 | 180 |
| 50 | 180 |
| 50 | 90 |
| 52 | 90 |

10. Add 60 ul of Enzyme Fragment Complementation (EFC) mix (containing EA, EA dilution buffer, lysis buffer and substrate); 11. Read plates after 30 min incubation at RT.
The assay metrics shown in Example 13 are for the condition where the Pulse temperature was 48° C. and the denaturation time was 90 seconds.

Example 14: In-Cell Method Using a Bromodomain Protein and its Inhibitor: FIG. 16

Assay Metrics (n=2)

| Inhibitor | $EC_{50}$ (nM) | Assay Window |
|---|---|---|
| JQ1 | 390 +/− 23 | 3.5 +/− 0.14 |

Published JQ1 cell potency for reducing c-Myc expression: $IC_{50}$≈100 nM, see Ciceri et al., "Dual kinase-bromodomain inhibitors for rationally designed polypharmacology," Nat Chem Biol. 2014 April; 10(4):305-12. doi: 10.1038/nchembio.1471. Epub 2014 Mar. 2.
Assay Protocol
BRD4(1) assay is performed essentially as described in previous example 13.

Example 15: In-Cell Method Using a Hydrolase and its Inhibitor: FIG. 17

Assay Metrics for SCH 51344 Binding

| Temp/Time | $EC_{50}$ (nM) | Assay Window |
|---|---|---|
| 45° C./1.5 min. | 370 | 1.9 |
| 48° C./3.0 min. | 4600 | 9.7 |

Published SCH 51344 MTH1 potency: Cellular $IC_{50}$<20 uM;
In vitro $EC_{50}$=50 nM.
Assay Protocol
MTH1 assay is performed essentially as follows:
MTH1 hydrolase catalytic domain expressed with a C-terminal PL tag and also fused at the N-terminus to the DNA binding domain of NF-κB was incubated for 3 hours with inhibitor at 37° C. followed by denaturation step as specified in Example 13.
For details on MTH1 and its inhibitor, see Huber et al., "Stereospecific targeting of MTH1 by (S)-crizotinib as an anticancer strategy," Nature 508, 222-227 (10 Apr. 2014) and Bessman et al., "The MutT Proteins or "Nudix" Hydrolases, a Family of Versatile, Widely Distributed, "Housecleaning" Enzymes," J. Biol. Chem. 271(41): 25059-25062 (1996).

Example 16: In-Cell Method Using G9a Methyltransferase and its Inhibitor: FIG. 18

Assay Metrics for UNC0538 Binding

| Inhibitor | $EC_{50}$ (nM) | Assay Window |
|---|---|---|
| UNC0538 | 13 | 5.0 |

Published UNC0538 cell potency for reducing H3K9me2: $IC_{50}$≈81 nM;
For details on methyltransferase and its inhibitor, see Vedadi et al., "A chemical probe selectively inhibits G9a and GLP methyltransferase activity in cells," Nature Chemical Biology 7, 566-574 (2011).
Assay Protocol
G9a assay is performed essentially as described for the previous Example. The G9a catalytic domain is expressed with a C-terminal PL tag.

A 3 hour incubation with inhibitor at 37° C. is followed by a single 3 minute denaturation step at 48° C.

CONCLUSION

The above specific description is meant to exemplify and illustrate the invention and should not be seen as limiting the scope of the invention, which is defined by the literal and equivalent scope of the appended claims. Any patents or publications mentioned in this specification are intended to convey details of methods and materials useful in carrying out certain aspects of the invention which may not be explicitly set out but which would be understood by workers in the field. Such patents or publications are hereby incorporated by reference to the same extent as if each was specifically and individually incorporated by reference and contained herein, for the purpose of describing and enabling the method or material referred to.

What is claimed is:

1. A method for measuring binding between a compound and a target macromolecule, comprising:
   (a) preparing a fluid mixture comprising (i) an intact viable cell expressing a chimeric protein that comprises a target macromolecule linked to a labeling peptide and (ii) a compound being measured for binding to the target macromolecule, wherein said target macromolecule is subject to denaturation;
   (b) incubating the fluid mixture of step (a) under conditions permitting binding of said compound to said target macromolecule;
   (c) denaturing target macromolecules in the fluid mixture, after incubating in step (b), under conditions that produce a combined mixture of (i) denatured chimeric molecules not bound to the compound and (ii) non-denatured chimeric molecules bound to the compound;
   (d) contacting the combined mixture of step (c) with a second label that binds to the labeling peptide to form a complex, wherein the complex occurs less with (i) denatured chimeric molecules not bound to the compound than with (ii) non-denatured chimeric molecules bound to the compound; and
   (e) detecting the complex in step (d) to generate a signal that indicates a measurement of binding between a compound and a target macromolecule.

2. The method of claim 1, wherein the target macromolecule is a protein.

3. The method of claim 2 wherein the protein further comprises an inactive exogenous polypeptide linked to the protein at a terminus distal to the labeling peptide.

4. The method of claim 3, wherein the labeling peptide is an epitope tag.

5. The method of claim 2, wherein the labeling peptide is between 10 and 100 amino acids in length.

6. The method of claim 5, wherein the labeling peptide is an enzyme fragment and the second label is a complementary enzyme fragment which combines with the labeling peptide to create an active enzyme, further comprising a step of lysing the cell.

7. The method of claim 6, wherein the labeling peptide is an enzyme donor ("ED") active in enzyme fragment complementation of β-galactosidase and is fused to a terminus of a protein that is the target macromolecule.

8. The method of claim 7, wherein the ED is one of SEQ ID NO: 1, SEQ ID NO: 2, or SEQ ID NO: 3.

9. The method of claim 1, wherein the compound is a small molecule.

10. The method of claim 9, wherein the small molecule is one that binds to an active site on the target macromolecule.

11. The method of claim 1, wherein the step of denaturing target macromolecules in the fluid mixture comprises a single step of heating the fluid mixture to a temperature that is from 25° C. to 100° C., or from 30° C. to 60° C.

12. The method of claim 1, wherein denaturing target macromolecules in the fluid mixture comprises multiple heating steps for a defined period of time between 0.1 and 5 minutes.

13. The method of claim 12, wherein said heating step comprises applying heat to the mixture between 40° C. and 60° C., and further comprises multiple steps of heating for a time of 0.1 to 5 minutes.

14. The method of claim 13, wherein multiple steps of heating comprises individual cooling steps between individual heating steps, of between 10 seconds and 2 minutes in duration.

15. The method of claim 1, wherein the step of denaturation comprises (a) heating, (b) hydrostatic pressure, (c) an organic solvent, (d) radiation, or any combination thereof, whereby the cell remains intact after denaturation.

16. The method of claim 5, wherein the organic solvent is alcohol or chloroform.

17. The method of claim 1 wherein steps (a) through (e) are carried out in mixtures containing different dilutions of said compound.

18. The method of claim 17, wherein repeated steps (a) through (e) may be used to calculate a binding constant ($K_D$) of binding of compound to the target macromolecule.

19. The method of claim 1, wherein the target macromolecule is a protein selected from the group consisting of a bromodomain protein, a protein kinase, a hydrolase, and a histone methyltransferase.

20. A method for measuring a binding property between a small molecule compound and a target protein, comprising:
   (a) preparing a fluid mixture comprising cells expressing a fusion of a target protein and a labeling peptide that is a β-galactosidase enzyme fragment of between 10 and 100 amino acids in length, said fluid mixture further containing a small molecule compound being measured for binding to the target protein;
   (b) incubating the fluid mixture of step (a) under conditions permitting binding of said small molecule compound to target proteins in the cell;
   (c) heating the fluid mixture of step (b), whereby denaturation of target proteins not bound to the compound occurs;
   (d) lysing cells heated in step (c) and adding to the mixture a second label that is a β-galactosidase fragment that reacts with the labeling peptide on non-denatured target proteins to a greater extent than labeling peptide on denatured target proteins, and further adding a substrate that substrate generates a signal indicative of a degree of denaturation of target proteins, whereby detecting said signal indicates binding between said small molecule and said target protein.

21. The method of claim 20, wherein a mixture is prepared through steps (a) to (d) in a single container.

22. The method of claim 20, wherein replicate samples containing different concentrations of compound are prepared.

23. The method of claim 20, wherein the target macromolecule is selected from the group consisting of a bromodomain protein and an enzyme.

* * * * *

SEQUENCE LISTING

```
<160> NUMBER OF SEQ ID NOS: 3

<210> SEQ ID NO 1
<211> LENGTH: 52
<212> TYPE: PRT
<213> ORGANISM: E. coli
<220> FEATURE:
<221> NAME/KEY: PEPTIDE
<222> LOCATION: (1)..(52)
<223> OTHER INFORMATION: Wild-type ED

<400> SEQUENCE: 1

Met Gly Val Ile Thr Asp Ser Leu Ala Val Val Leu Gln Arg Arg Asp
1               5                   10                  15

Trp Glu Asn Pro Gly Val Thr Gln Leu Asn Arg Leu Ala Ala His Pro
            20                  25                  30

Pro Phe Ala Ser Trp Arg Asn Ser Glu Glu Ala Arg Thr Asp Arg Pro
        35                  40                  45

Ser Gln Gln Leu
    50

<210> SEQ ID NO 2
<211> LENGTH: 42
<212> TYPE: PRT
<213> ORGANISM: E. coli
<220> FEATURE:
<221> NAME/KEY: PEPTIDE
<222> LOCATION: (1)..(42)
<223> OTHER INFORMATION: ProLabel ED

<400> SEQUENCE: 2

Asn Ser Leu Ala Val Val Leu Gln Arg Arg Asp Trp Glu Asn Pro Gly
1               5                   10                  15

Val Thr Gln Leu Asn Arg Leu Ala Ala His Pro Pro Phe Ala Ser Trp
            20                  25                  30

Arg Asn Ser Glu Glu Ala Arg Thr Asp Arg
        35                  40

<210> SEQ ID NO 3
<211> LENGTH: 52
<212> TYPE: PRT
<213> ORGANISM: E. coli
<220> FEATURE:
<221> NAME/KEY: PEPTIDE
<222> LOCATION: (1)..(52)
<223> OTHER INFORMATION: W34Y ED

<400> SEQUENCE: 3

Met Gly Val Ile Thr Asp Ser Leu Ala Val Val Leu Gln Arg Arg Asp
1               5                   10                  15

Trp Glu Asn Pro Gly Val Thr Gln Leu Asn Arg Leu Ala Ala His Pro
            20                  25                  30

Pro Phe Ala Ser Tyr Arg Asn Ser Glu Glu Ala Arg Thr Asp Arg Pro
        35                  40                  45
```

Ser Gln Gln Leu
    50